(12) United States Patent
Skwarek et al.

(10) Patent No.: US 8,048,069 B2
(45) Date of Patent: Nov. 1, 2011

(54) USER INTERFACE FOR ABLATION THERAPY

(75) Inventors: Thomas R. Skwarek, Shoreview, MN (US); William K. Wenger, St. Paul, MN (US); Keith S. Bosacker, St. Anthony, MN (US)

(73) Assignee: Medtronic, Inc., Minneapolis, MN (US)

( * ) Notice: Subject to any disclaimer, the term of this patent is extended or adjusted under 35 U.S.C. 154(b) by 1236 days.

(21) Appl. No.: 11/787,211

(22) Filed: Apr. 13, 2007

(65) Prior Publication Data

US 2008/0082145 A1 Apr. 3, 2008

Related U.S. Application Data

(60) Provisional application No. 60/848,599, filed on Sep. 29, 2006.

(51) Int. Cl.
*A61B 18/18* (2006.01)
(52) U.S. Cl. .......................... 606/38; 606/34
(58) Field of Classification Search .............. 606/34, 606/37, 38
See application file for complete search history.

(56) References Cited

U.S. PATENT DOCUMENTS

| | | |
|---|---|---|
| 3,124,373 A | 3/1964 | Thomsen |
| 3,929,356 A | 12/1975 | DeVincent et al. |
| 4,269,075 A | 5/1981 | Crist et al. |
| 4,931,040 A | 6/1990 | Haber et al. |
| 5,026,016 A | 6/1991 | Lisowski |
| 5,345,362 A | 9/1994 | Winkler |
| 5,435,805 A | 7/1995 | Edwards et al. |
| 5,454,782 A | 10/1995 | Perkins |
| 5,458,597 A | 10/1995 | Edwards et al. |
| 5,470,308 A | 11/1995 | Edwards et al. |
| 5,472,441 A | 12/1995 | Edwards et al. |
| 5,507,743 A | 4/1996 | Edwards et al. |

(Continued)

FOREIGN PATENT DOCUMENTS

DE 4 209 000 5/1993

(Continued)

OTHER PUBLICATIONS

Birch et al., "Transurethral Resection of Prostate Under Sedation and Local Anesthesia (Sedoanalgesia)," Urology, Aug. 1991, vol. XXXVIII, No. 2., pp. 113-118.

(Continued)

*Primary Examiner* — Linda Dvorak
*Assistant Examiner* — Jaymi Della
(74) *Attorney, Agent, or Firm* — Scott A. Marks; Schumaker & Sieffert, P.A.

(57) ABSTRACT

The disclosure describes a user interface that may be used to control ablation therapy and monitor ablation therapy progress in systems that utilize wet electrode ablation techniques. The user interface presents a virtual electrode depth icon to a user that indicates the size of a lesion that may be created with the selected virtual electrode depth. The virtual electrode depth may be changed by the user according to the ablation therapy most appropriate for a patient, and the user may interact with the user interface to define the virtual electrode depth. In this manner, the user interface may be a touchscreen or other input device such as a mouse, pointing device, or keyboard. The user interface may also provide a thermometer icon that represents a patient temperature, a timer icon that represents a remaining time for therapy, and other representations of therapy progress.

15 Claims, 13 Drawing Sheets

U.S. PATENT DOCUMENTS

| | | | |
|---|---|---|---|
| 5,531,676 A | 7/1996 | Edwards et al. | |
| 5,536,267 A | 7/1996 | Edwards et al. | |
| 5,540,681 A * | 7/1996 | Strul et al. | 606/34 |
| D373,193 S | 8/1996 | Luther | |
| 5,582,588 A | 12/1996 | Sakurai et al. | |
| D394,903 S | 6/1998 | Barkley et al. | |
| 5,788,291 A | 8/1998 | Williams et al. | |
| 5,807,395 A * | 9/1998 | Mulier et al. | 606/41 |
| 5,827,280 A | 10/1998 | Sandock et al. | |
| D402,758 S | 12/1998 | Barkley et al. | |
| 5,865,788 A | 2/1999 | Edwards et al. | |
| 5,871,481 A | 2/1999 | Kannenberg et al. | |
| D411,622 S | 6/1999 | Hall | |
| 5,964,756 A | 10/1999 | McGaffigan et al. | |
| 5,995,875 A | 11/1999 | Blewett et al. | |
| 6,071,280 A | 6/2000 | Edwards et al. | |
| 6,090,105 A | 7/2000 | Zepeda et al. | |
| 6,106,521 A | 8/2000 | Blewett et al. | |
| 6,113,594 A | 9/2000 | Savage | |
| 6,113,597 A | 9/2000 | Eggers et al. | |
| 6,129,726 A | 10/2000 | Edwards et al. | |
| D438,204 S | 2/2001 | Winkler | |
| D441,450 S | 5/2001 | Salvatori et al. | |
| 6,231,591 B1 | 5/2001 | Desai | |
| 6,238,393 B1 | 5/2001 | Mulier et al. | |
| 6,241,702 B1 | 6/2001 | Lundquist et al. | |
| 6,241,725 B1 * | 6/2001 | Cosman | 606/41 |
| D447,241 S | 8/2001 | Deck | |
| 6,280,440 B1 | 8/2001 | Gocho | |
| 6,302,903 B1 | 10/2001 | Mulier et al. | |
| 6,315,777 B1 | 11/2001 | Comben | |
| 6,322,558 B1 | 11/2001 | Taylor et al. | |
| 6,327,492 B1 | 12/2001 | Lemelson | |
| 6,402,742 B1 | 6/2002 | Blewett et al. | |
| 6,409,722 B1 | 6/2002 | Hoey et al. | |
| 6,461,296 B1 | 10/2002 | Desai | |
| 6,464,661 B2 | 10/2002 | Edwards et al. | |
| 6,471,698 B1 | 10/2002 | Edwards et al. | |
| 6,497,705 B2 | 12/2002 | Comben | |
| 6,506,189 B1 * | 1/2003 | Rittman et al. | 606/41 |
| 6,514,247 B1 | 2/2003 | McGaffigan et al. | |
| 6,526,320 B2 | 2/2003 | Mitchell | |
| D471,279 S | 3/2003 | Locke et al. | |
| 6,537,248 B2 | 3/2003 | Mulier et al. | |
| 6,537,272 B2 | 3/2003 | Christopherson et al. | |
| 6,551,300 B1 | 4/2003 | McGaffigan | |
| 6,575,969 B1 * | 6/2003 | Rittman et al. | 606/41 |
| 6,580,948 B2 | 6/2003 | Haupert et al. | |
| 6,623,515 B2 | 9/2003 | Mulier et al. | |
| 6,632,221 B1 | 10/2003 | Edwards et al. | |
| 6,632,222 B1 | 10/2003 | Edwards et al. | |
| 6,638,275 B1 | 10/2003 | McGaffigan et al. | |
| 6,641,580 B1 | 11/2003 | Edwards et al. | |
| 6,642,274 B1 | 11/2003 | Neal | |
| 6,645,202 B1 | 11/2003 | Pless et al. | |
| 6,652,516 B1 | 11/2003 | Gough | |
| 6,659,105 B2 | 12/2003 | Burbank et al. | |
| 6,659,106 B1 | 12/2003 | Hovda et al. | |
| 6,669,685 B1 | 12/2003 | Rizoiu et al. | |
| 6,671,558 B1 | 12/2003 | Soykan et al. | |
| D484,981 S | 1/2004 | Faller et al. | |
| 6,673,063 B2 | 1/2004 | Brett | |
| 6,676,658 B2 | 1/2004 | Burbank et al. | |
| 6,678,554 B1 | 1/2004 | Sun et al. | |
| 6,685,702 B2 | 2/2004 | Quijano et al. | |
| 6,689,128 B2 | 2/2004 | Sliwa, Jr. et al. | |
| 6,690,976 B2 | 2/2004 | Fenn et al. | |
| 6,706,039 B2 | 3/2004 | Mulier et al. | |
| 6,719,755 B2 | 4/2004 | Sliwa, Jr. et al. | |
| 6,761,715 B2 | 7/2004 | Carroll | |
| 6,764,487 B2 | 7/2004 | Mulier et al. | |
| 6,805,128 B1 | 10/2004 | Pless et al. | |
| 6,805,129 B1 | 10/2004 | Pless et al. | |
| D499,183 S | 11/2004 | Vaisnys et al. | |
| 6,814,712 B1 | 11/2004 | Edwards et al. | |
| 6,849,073 B2 | 2/2005 | Hoey et al. | |
| 6,852,091 B2 | 2/2005 | Edwards et al. | |
| 6,855,141 B2 | 2/2005 | Lovewell | |
| 6,932,811 B2 * | 8/2005 | Hooven et al. | 606/41 |
| D509,900 S | 9/2005 | Barnes et al. | |
| 6,989,004 B2 | 1/2006 | Hinchliffe et al. | |
| D538,432 S | 3/2007 | Diener et al. | |
| 2001/0031941 A1 | 10/2001 | Edwards et al. | |
| 2001/0039415 A1 | 11/2001 | Francischelli et al. | |
| 2001/0056226 A1 | 12/2001 | Zodnik et al. | |
| 2002/0026188 A1 * | 2/2002 | Balbierz et al. | 606/41 |
| 2002/0058933 A1 * | 5/2002 | Christopherson et al. | 606/34 |
| 2002/0111548 A1 | 8/2002 | Swanson et al. | |
| 2002/0111619 A1 | 8/2002 | Keast et al. | |
| 2002/0128643 A1 | 9/2002 | Simpson et al. | |
| 2002/0151884 A1 | 10/2002 | Hoey et al. | |
| 2002/0173721 A1 | 11/2002 | Grunwald et al. | |
| 2002/0177846 A1 | 11/2002 | Mulier et al. | |
| 2002/0183740 A1 | 12/2002 | Edwards et al. | |
| 2003/0028188 A1 | 2/2003 | Paddock et al. | |
| 2003/0073989 A1 | 4/2003 | Hoey et al. | |
| 2003/0093503 A1 | 5/2003 | Yamaki et al. | |
| 2003/0103932 A1 | 6/2003 | Slepian et al. | |
| 2003/0130711 A1 * | 7/2003 | Pearson et al. | 607/101 |
| 2003/0171672 A1 * | 9/2003 | Varghese et al. | 600/420 |
| 2004/0002647 A1 | 1/2004 | Desai | |
| 2004/0082946 A1 | 4/2004 | Malis et al. | |
| 2004/0133194 A1 | 7/2004 | Eum et al. | |
| 2004/0172112 A1 | 9/2004 | Cioanta et al. | |
| 2005/0245923 A1 * | 11/2005 | Christopherson et al. | 606/41 |
| 2006/0089636 A1 | 4/2006 | Christopherson et al. | |
| 2006/0270916 A1 | 11/2006 | Skwarek et al. | |

FOREIGN PATENT DOCUMENTS

| | | |
|---|---|---|
| EP | 1 818 021 A1 | 8/2007 |
| WO | WO 00/66015 | 11/2000 |

OTHER PUBLICATIONS

Leveillee et al., "Radiofrequency Interstitial Tissue Ablation: Wet Electrode;" Journal of Endourology, vol. 17, No. 8, pp. 563-577, 2003.

Related patent application entitled "Delivery of Fluid During Transurethral Prostate Treatment", U.S. Appl. No. 10/424,040, filed Apr. 24, 2003, now abandoned.

Related patent application entitled "Bipolar Virtual Electrode for Transurethral Needle Ablation", U.S. Appl. No. 10/835,193, filed Apr. 29, 2004, now abandoned.

U.S. Patent Application entitled "User Interface for a Portable Therapy Delivery Device", U.S. Appl. No. 11/414,623, filed Apr. 28, 2006, Skwarek et al.

U.S. Patent Application entitled "Operation Indicator for a Portable Therapy Delivery Device", U.S. Appl. No. 11/414,501, filed Apr. 28, 2006, Skwarek et al.

Notification of Transmittal of the International Search Report and the Written Opinion of the International Searching Authority, or the Declaration, for corresponding patent application No. PCT/US2007/077506, mailed Apr. 29, 2008, 14 pages.

Office Action dated Nov. 30, 2009 for U.S. Appl. No. 11/241,825 (26 pgs.).

Request for Continued Examination and Amendment dated Feb. 1, 2010 for U.S. Appl. No. 11/241,825 (31 pgs.).

\* cited by examiner

USER INTERFACE FOR ABLATION THERAPY

This application claims the benefit of U.S. Provisional Application No. 60/848,599, filed Sep. 29, 2006, the entire content of each of which is incorporated herein by reference.

TECHNICAL FIELD

The invention relates to medical devices and, more particularly, to user interfaces for controlling and monitoring therapy delivery.

BACKGROUND

Ablation therapy is a surgical technique used to destroy or remove tissue selectively to reduce or eliminate patient conditions. Many different technologies are directed to tissue ablation. Such technologies include electrical ablation, ultrasound ablation, cryoablation, conductive heating, radioactive heating, and combination ablation that includes more than one technology. Electrical ablation includes radio frequency (RF) ablation, microwave ablation, and other electrical ablation technologies that utilize electrical current to heat the target tissue. Another electrical ablation technique includes RF ablation and a fluid medium to heat and ablate the tissue. This technique utilizes devices commonly called "wet electrodes" which pass electrical current from the electrodes through an adjacent fluid. All of these techniques require user input to control the ablation therapy.

Ablation therapy systems commonly include user interfaces that allow a user to define the parameters of the ablation therapy, monitor the ablation therapy progress, or both. These user interfaces may include simple switches and dials, individual electrical inputs and outputs, complex user interfaces such as cathode ray tubes (CRT) or liquid crystal displays (LCD), or a combination of these types of controls. The user interacts with the user interface to correctly deliver ablation therapy to the patient and monitor progress to stop therapy before ablating healthy tissue or otherwise harming the patient. In some cases, user interfaces are directed to a particular patient anatomy or ablation therapy.

One example of an ablation therapy is treatment for benign prostatic hyperplasia (BPH). BPH is a condition caused by the second period of continued prostate gland growth. This growth begins after a man is approximately 25 years old and may begin to cause health problems after 40 years of age. The prostate growth eventually begins to constrict the urethra and may cause problems with urination and bladder functionality. Ablation therapy attempts to create a lesion in the prostate and decrease the prostate size, restoring appropriate bladder function.

SUMMARY

The disclosure describes a user interface that may be used to control ablation therapy and monitor ablation therapy progress in systems that utilize wet electrode ablation techniques. The user interface presents a virtual electrode depth icon to a user that indicates the size of a lesion that may be created with the selected virtual electrode depth. The virtual electrode depth icon may include a plurality of nested circles or a spiral ramped depth. The virtual electrode depth may be changed by the user according to the ablation most appropriate for a patient or therapy, and the user may interact with the user interface to define the virtual electrode depth. During ablation therapy, the virtual electrode depth icon is progressively shaded to represent the current lesion size already created.

The user interface may also provide other data to the user. For example, a thermometer icon that represents a therapy critical temperature may be displayed that allows the user to quickly identify the temperature of sensitive tissue adjacent to the lesion area. In addition, the user interface may display a remaining time for ablation therapy, an electrical resistance indicator for the ablated tissue, and other therapy indicators such as fluid pressure.

The user interface controls the ablation system that creates the lesion in the patient. In this manner, the user interface may be embodied as a touchscreen that makes changes to the therapy according to where the user presses on the touchscreen. However, other input devices such as a mouse, pointing device, keyboard, or voice activation device may be implemented with the user interface. As described herein, the example user interface is optimized to ablate prostate tissue with a wet electrode. However, the user interface may be used with any type of ablation procedure.

In one embodiment, this disclosure is directed to a method that includes receiving ablation user input from a user defining a virtual electrode depth. The method also includes representing the virtual electrode depth of an ablation device as a virtual electrode depth icon on a display, wherein the virtual electrode depth icon is configured to progressively shade an area of the virtual electrode depth according to an ablation therapy progress.

In another embodiment, this disclosure is directed to a system that includes a user interface that represents a virtual electrode depth of an ablation device as a virtual electrode depth icon and receives ablation user input from a user, wherein the virtual electrode depth icon is configured to progressively shape an area of the virtual electrode depth icon according to an ablation therapy progress. The system also includes a processor that defines the virtual electrode depth according to the ablation user input.

In an additional embodiment, this disclosure is directed to a computer-readable medium including instructions that cause a processor to receive ablation user input from a user defining a virtual electrode depth. The computer-readable medium also includes instructions that cause the processor to represent a virtual electrode depth of an ablation device as a virtual electrode depth icon on a display. The virtual electrode depth icon is configured to progressively shade an area of the virtual electrode depth according to an ablation therapy.

In various embodiments, the device described in this disclosure may provide one or more advantages. For example, the user interface displays a simple virtual electrode depth icon that indicates the size of a lesion that will be produced during the ablation therapy. The virtual electrode depth icon progressively shades the predicted lesion size during therapy to indicate the lesion progress. In addition, the user interface provides a thermometer icon that includes multiple methods for viewing a tissue temperature including thermometer icon color, a slider on the icon, and a number value for the temperature. In this manner, the user interface may reduce the time needed by a user to set up the therapy and enable more efficient therapy delivery.

The details of one or more embodiments of the invention are set forth in the accompanying drawings and the description below. Other features, objects, and advantages of the invention will be apparent from the description and drawings, and from the claims.

DETAILED DESCRIPTION

This disclosure is directed to a user interface and methods for representing ablation therapy parameters of an ablation system to a user in a simple and easy to view format. The user interface allows the user to adjust a virtual electrode depth (VED) of the ablation system and represents the VED as a virtual electrode depth icon (VED icon). The virtual electrode depth may relate to the depth of a needle electrode created by energy conductive fluid surrounding the actual needle electrode within the patient. The VED icon may include a plurality of nested circles that indicate the size, or volume, of a lesion that will be created with ablation therapy at the current VED value. As ablation therapy progresses, the circles of the VED icon will be progressively shaded from the middle of the smallest circle outwards to the largest circle. In other examples, the VED icon may provide the virtual electrode depth information in a manner different than the nested circles, as further discussed below.

In addition to the VED icon, the user interface may include other indications of ablation therapy parameters or ablation progress. For example, the user interface may display the remaining time to complete the current lesion and include a thermometer to monitor at the temperature of non-ablation tissue. Other elements of the user interface may include tissue electrical resistance, status messages, or other appropriate indicators.

The user interface is directed to wet electrode ablation therapy of the prostate in the examples of this disclosure. However, the user interface may be utilized by other ablation technologies such as microwave ablation, cryoablation, ultrasound ablation, and conductive heating ablation. In addition, the wet electrode ablation, or other ablation technique, may be used on a tissue other than the prostate. For example, the ablation therapy may be directed to an internal tissue such as cardiac tissue, ovarian cysts, colon polyps, tumors, or any other tissue of a patient. However, exposed tissue may also be treated with this user interface. As described herein, a user may be a physician, a clinician, a certified technician, or anyone trained to use ablation system 10.

Figure 1:
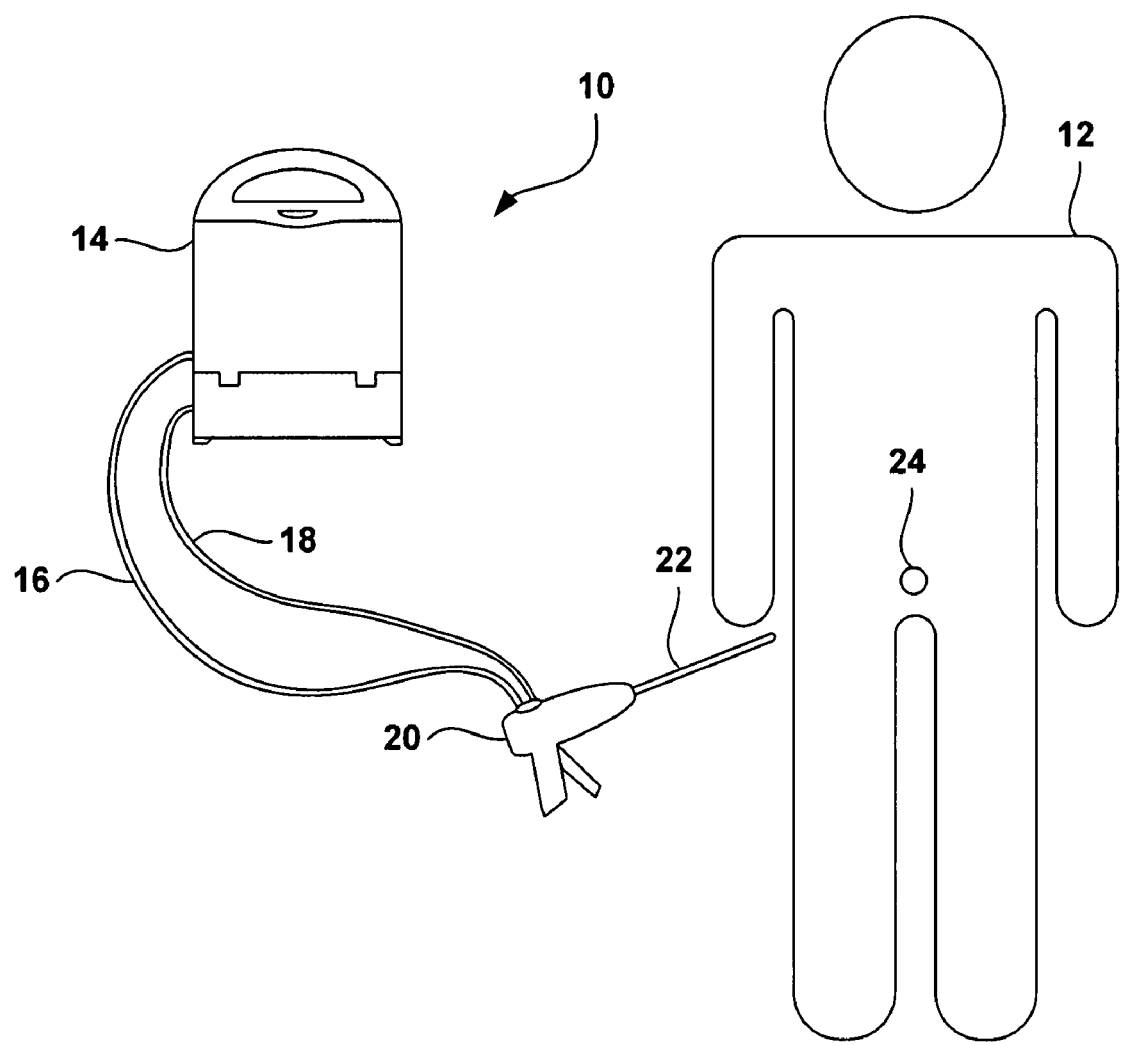
FIG. 1 is a conceptual diagram illustrating an example ablation system in conjunction with a patient.

FIG. 1 is a conceptual diagram illustrating an example ablation system in conjunction with a patient. As shown in FIG. 1, ablation system 10 may include a portable therapy delivery device (PTD) 14 that delivers therapy to treat a condition of patient 12. In this exemplary embodiment, PTD 14 is a radio frequency (RF) generator that provides RF energy to heat tissue of the prostate gland 24. This ablation of prostate tissue destroys a portion of the enlarged prostate caused by, for example, benign prostatic hyperplasia (BPH). The RF energy is transmitted through electrical cable 16 to ablation device 20. The energy is then transmitted through a probe 22 and is delivered to prostate 24 by an electrode (not shown). In addition to the electrode, a fluid may be pumped out of PTD 14, through tube 18, into ablation device 20, and through probe 22 to interact with the RF energy being delivered by the electrode. This wet electrode may increase the effective heating area of the electrode and increase therapy efficacy. Specifically, the effective heating area may be increased or decreased by changing the flow rate of fluid from PTD 14. Alternatively, the shape of the produced lesion may be changed by the type of delivered fluid from the wet electrode or shape and dimensions of the needle electrode. For example, cooled saline or a hypertonic fluid may be used to alter the generally spherical shape of the lesion.

In the illustrated example, PTD 14 includes an RF generator that includes circuitry for developing RF energy from an included rechargeable battery or drawn from a common electrical outlet. The RF energy is produced within defined ablation parameters to provide appropriate prostate tissue heating. PTD 14 also includes a user interface (not shown) that allows a user to control the ablation therapy when the screen of PTD is opened to show the user interface to the user.

Therapy energy and other associated functions such as fluid flow are controlled via the user interface located on a color liquid crystal display (LCD), or equivalent screen. The screen may provide images created by the therapy software, and the user may interact with the software by touching the screen at certain locations indicated by the user interface. In this embodiment, no additional devices, such as a keyboard or pointer device, are needed to interact with the device. The touch screen may also enable device operation.

The touchscreen of the user interface may be a liquid crystal display (LCD) touch screen. The physician may interact with the screen by using a finger or stylus to touch the screen where certain icons appear. In this manner, the physician may control the therapy and PTD operation without the use of additional keyboards or pointer devices. The screen may utilize any type of touch screen technology that allows the physician to select icons or graphics on the screen with a finger, stylus, or gloved finger. These types of technologies include, but are not limited to resistive systems, capacitive systems, and acoustic wave systems.

In some embodiments, the device may require an access code or biometric authorization to use the device. Requiring the physician to provide a fingerprint, for example, may limit unauthorized use of the system. In other embodiments, the user interface may include a pointing device, a keyboard, a joystick, or other input device. In alternative embodiments, the user interface may accept verbal commands from the user.

Connected to PTD 14 are one cable 16 and one tube 18. Cable 16 conveys RF energy and tube 18 conducts fluid from PTD 14 to ablation device 20. Ablation device 20 may be embodied as a hand-held device as shown in FIG. 1. Ablation device 20 may include a trigger to control the start and stop of therapy. The trigger may be pressure sensitive, where increased pressure of the trigger provides an increased amount of RF energy or increase the fluid flow to the tissue of prostate 24. This type of feature may be enabled by the user interface. Attached to the distal end of ablation device 20 is a probe 22. The probe may provide a conduit for the fluid and provide isolation between one or more needles that conduct RF energy and patient 12. Since the probe 22 would be entering patient 12 through the urethra, the probe may be very thin in diameter and long enough to reach the prostate in any patient.

Probe 22 may contain one or more electrodes for delivering RF current to the tissue of enlarged prostate 24. Probe 22 may contain one or more needles, each with an electrode, for penetrating into two areas of prostate 24 from the urethra. The areas may be adjacent to each other or separated into opposing areas. When RF energy is being delivered, tissue may increase in temperature, which destroys a certain volume of tissue. This heating may last a few seconds or a few minutes, depending on the condition of prostate 24 and the desired therapy. In some embodiments, the fluid may exit small holes in the needles and flow around the electrodes. In other embodiments, the fluid may enter the patient through a different mechanism than holes in the needles. For example, the fluid may pass through a permeable member, along a sheath, or via another element that distributes the fluid in a desired manner. Alternatively, a different probe or needle than the electrode may deliver the fluid. This conducting fluid, e.g., saline, may increase the effective heating area and decrease the heating time. Additionally, ablating tissue in this manner may enable the physician to complete therapy without repositioning the needle or using different sized needles.

In some cases, ablation devices may only be used for one patient. Reuse may cause infection and contamination, so it may be desirable for the ablation device to only be used once. A feature on the ablation device may be a smart chip in communication with the PTD 14. The smart chip of the device may trigger the processor of PTD 14 to load a specific software application that utilizes the connected device. As another example, when the ablation device is connected to PTD 14, the PTD may request use information from the ablation device. If the device has been used before, the PTD may disable all functions of the ablation device to prevent reuse of the device. This determination may be presented to the user via the user interface as a warning or an error message. The user interface may suggest a course of action for the user. Once an ablation device has been used, the smart chip may create a use log to identify the therapy delivered and record that the device has been used. The log may include data of RF energy delivered to the patient, total RF energy delivered in terms of joules or time duration, error messages created, or any other pertinent information. In some embodiments, the user may utilize the user interface to modify the information stored in the log.

In some embodiments, additional peripheral accessories, i.e., therapy devices or diagnostic devices, may be available to the physician at one time. For example, the ablation device for ablating prostate tissue might be coupled with an endoscopic camera for locating the prostate and monitoring therapy. The camera images may then be transferred back to PTD 14 and presented on the screen in real-time. Other examples may include ultrasound imaging coupled with ablation therapy or programming implanted medical devices. The flexible platform of the PTD 14 may allow various diagnostic and therapy combinations to be combined into one device. In these cases, the user interface may be adapted to include these functions within the same delivery screen or require the user toggle between two or more screens to access control or to monitor the additional function.

While PTD 14 is described as a small portable device, the PTD could be embodied as any type of system that supports ablation therapy as described herein. For example, PTD 14 may be an RF generator controlled by a notebook computer. Alternatively, PTD 14 may be a large stationary ablation system that provides a large monitor on top of a stack of components of the system. In other embodiments, PTD 14 may only be the ablation component of a more comprehensive system that supports other functions or therapies separate from the ablation therapy. In any case, PTD 14 is only described herein as an exemplary embodiment of the ablation system which includes the user interface.

Figure 2:
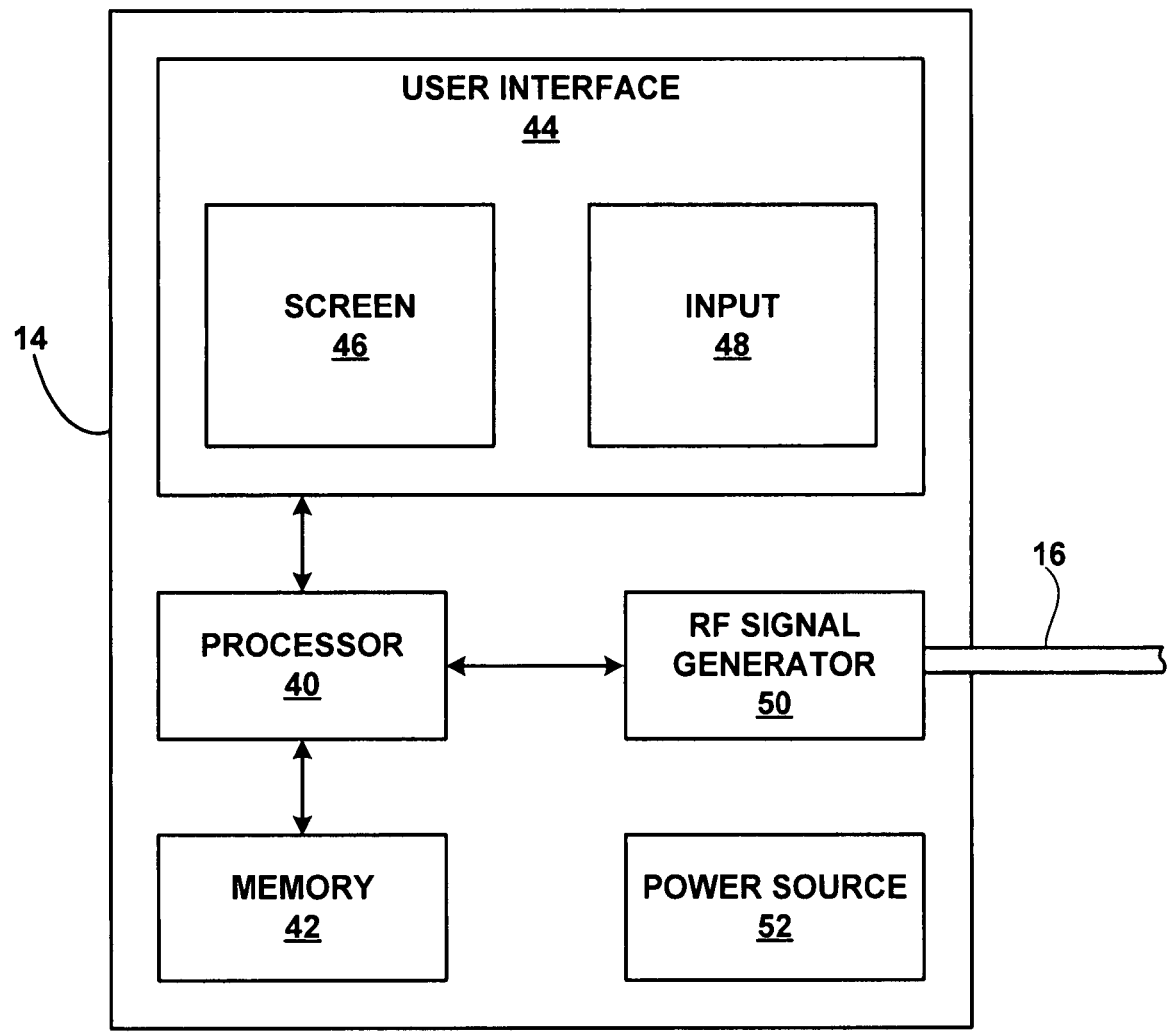
FIG. 2 is functional block diagram illustrating components of an exemplary ablation system that supports the user interface.

FIG. 2 is functional block diagram illustrating components of an exemplary ablation system that supports the user interface. In the example of FIG. 2, PTD 14 includes a processor 40, memory 42, user interface 44, screen 46, input 48, RF signal generator 50, and power source 52. Cable 16 is connected to RF signal generator 50 and ablation device 20 (not shown). PTD 14 may include other components not shown in FIG. 2, such as a fluid pump for delivering fluid to ablation device 20 to create the wet electrode.

Processor 40 controls RF signal generator 50 to deliver RF energy therapy according to therapy parameters, such as VED values defined through user interface 44. Processor 40 uses instructions stored in memory 42 to support user interface 44. As described herein, user interface 44 includes screen 46 and input 48 combined into a touchscreen. Other embodiments may have less integrated user interfaces, such as an output screen and separate pointing device that is input 48.

Processor 40 may also control data flow from the therapy. Data such as RF energy produced, temperature of tissue, and fluid flow may be channeled into memory 42 for analysis. In addition, any data collected from patient 12 using the given sensor configuration may be stored in memory 42. Processor 40 may comprise any one or more of a microprocessor, digital signal processor (DSP), application specific integrated circuit (ASIC), field-programmable gate array (FPGA), or other digital logic circuitry. Memory 42 may include multiple memories for storing a variety of data. For example, one memory may contain therapy parameters, one may contain PTD operational files, and one may contain therapy data. The instructions for user interface 44 may be included in PTD operation files. Memory 42 may include any one or more of a random access memory (RAM), read-only memory (ROM), electronically-erasable programmable ROM (EEPROM), flash memory, or the like.

In a preferred embodiment, the RF signal generator may have certain performance parameters. In this exemplary case, the generator may provide RF energy into two delivery channels with a maximum of 50 Watts per channel. Other embodiments may include generation in excess of 100 watts for one channel. Duty cycles of the energy may alter the total power capable of being produced. In other examples, the ramp time for a 50 Watt change in power may occur in less than 25 milliseconds, and the output power may be selected in 1 Watt steps. The maximum current to be provided to the patient may be 2 Amps, and the maximum voltage may be 180 Volts. Other embodiments of the signal generator may have different power capabilities, e.g. current and voltage maximums, as needed by the intended use of PTD 14.

User interface 44 may also control communications between PTD 14 and other devices. Communications with PTD 14 may be accomplished by radio frequency (RF) communication or local area network (LAN) with another computing device or network access point. This communication is possible through the use of communication interface (not shown). The communication interface may be configured to conduct wireless or wired data transactions simultaneously as needed by a user, e.g., a physician or clinician.

PTD 14 may communicate with a variety of devices to enable appropriate operation such as to monitor inventory, order disposable parts for therapy from a vendor, and download upgraded software for a therapy. In some embodiments, the physician may communicate with a help-desk, either computer directed or human staffed, in real-time to solve operational problems quickly. These problems with PTD 14 or a connected ablation device may be diagnosed remotely and remedied via a software patch in some cases.

Screen 46 is the interface between PTD 14 and the physician. Processor 40 controls the graphics displayed on screen 46 and identifies when the physician presses on certain portions of the screen 46, which is input 48. In this manner, user interface 44 is central to the control of therapy, diagnosis, and other functions supported in PTD 14.

As described above, screen 46 may be integrated with input 48 as a touchscreen. In this manner, user interface 44 may utilize any type of touchscreen system. One example of a touch screen is a resistive system to detect the location of a touch on the screen. The resistive system consists of a normal glass panel that is covered with a conductive and a resistive metallic layer. The conductive and resistive layers are separated by spacers with a scratch-resistant layer disposed on the surface of screen 46. An electrical current flows through the conductive and resistive layers when screen 46 is operational. When the physician touches the screen, the conductive layer contacts the resistive layer on the location of the touch. The change in the electrical field is detected by screen 46 and the coordinates of the location is calculated by a processor. Once the coordinates are calculated, a driver translates the location into data that the operating system uses to control PTD 14.

In some embodiments of screen 46, screen 46 may utilize a capacitive system. The capacitive system includes a capacitive layer that stores electrical charge that is placed on a glass panel of screen 46. When the physician touches the monitor with a finger, a portion of the electrical charge is transferred to the physician. This transfer of electrical charge reduces the charge in the capacitive layer. A plurality of circuits located at each corner of screen 46 measures the decrease in charge, and a processor calculates the location of the touch from the relative differences in electrical charge at each corner of the screen. Screen 46 may be brighter when using the capacitive system as compared to the resistive system, but insulating objects may not be detected by the screen.

In alternative embodiments, screen 46 utilizes a surface acoustic wave system to detect touch on the screen. Two transducers, one receiving transducer and one sending transducer, are placed along an x axis and a y axis of the glass plate of screen 46. A plurality of reflectors are also placed on the glass plate to reflect an electrical signal sent from one transducer to the other transducer. The receiving transducer detects any disturbance in the sending wave from a touch to screen 46 and determines the location of the disturbance. The surface acoustic wave system contains no metallic layers, which allows almost all light to be delivered from screen 46 to the physician.

Power source 52 delivers operating power to the components of PTD 14. Power source 52 may utilize electricity from a standard 115 Volt electrical outlet or include a battery and a power generation circuit to produce the operating power. In other embodiments, power source 52 may utilize energy from any outlet that provides between 100 and 240 Volts. In some embodiments, the battery may be rechargeable to allow extended operation. Recharging may be accomplished through the 115 Volt electrical outlet. In other embodiments, traditional batteries may be used.

In some embodiments, signal generator 50 may be a different type of energy source. For example, the energy source may convert power from power source 52 to produce steam, mechanical energy, or any other type of output that may perform therapy on patient 12. Other energy may be laser energy or ultrasound energy. In this manner, the energy source may produce electrical, chemical, or mechanical energy.

Figure 3:
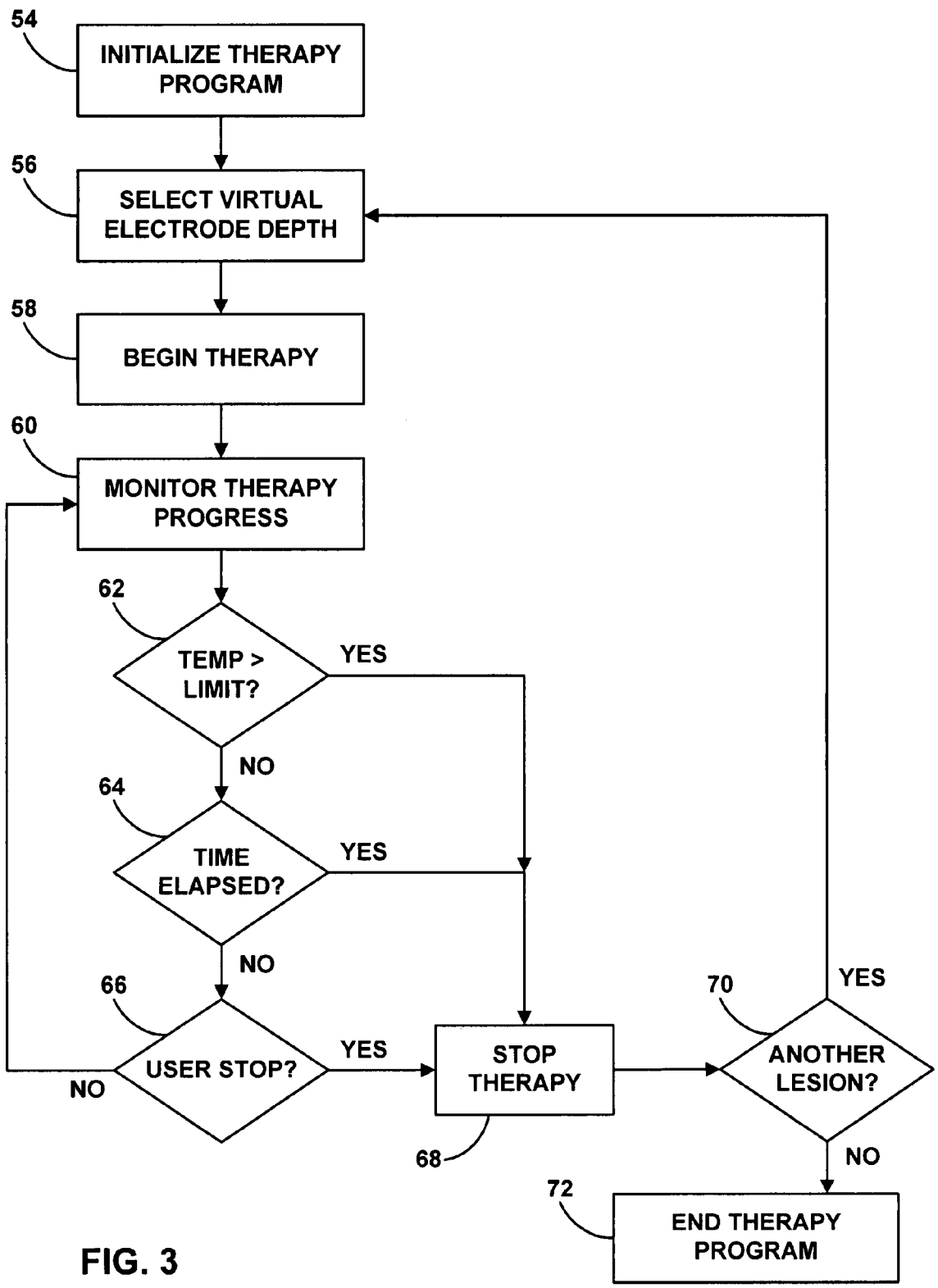
FIG. 3 is a flow diagram illustrating an example technique for operating the ablation system using the user interface.

FIG. 3 is a flow diagram illustrating an example technique for operating the ablation system using the user interface. As shown in FIG. 3, a user uses user interface 100 (of FIGS. 4-13) to deliver ablation therapy to patient 12. User interface 100 first allows the user to access the desired program by initializing the selected therapy program as directed by the user (54). User interface 100 next may receive ablation user input that selects, or defines, the virtual electrode depth (VED) value for the therapy (56). The ablation user input may be received from one or more interactive features of user interface 100. Once the user is prepared, user interface 100 begins the ablation therapy when directed by the user (58).

During the ablation therapy, user interface 100 monitors lesion progress for the user by representing lesion size, tissue electrical resistance, and urethral temperature (60). User interface 100 includes several mechanisms to stop the therapy. If the urethral temperature reaches a predetermined limit or threshold (62), user interface 100 automatically stops ablation therapy (68). Otherwise, therapy continues unless the ablation time has elapsed (64). If the time has elapsed, ablation therapy stops (68) and user interface 100 indicates that the therapy has stopped. In addition, user interface 100 may stop ablation therapy when directed by the user. If the user has directed ablation to stop (66), user interface 100 stops the therapy (68). If the user has not indicated that therapy should stop, therapy continues and user interface 100 continues to monitor therapy progress (60).

After ablation therapy has been stopped, user interface 100 may wait for the user to decide if another lesion is necessary to treat patient 12 (70). If another lesion is desired, user interface 100 enables the user to select a new VED value for the next lesion (56). If no more lesions are requested, the user may end the therapy program session through the use of user interface 100 (72).

In other embodiments, the chain of events may occur in a different sequence or include more or less options. For example, the user may need to define more parameters before ablation therapy may begin. Alternatively, the user may access other help menus when defining the therapy. User interface 100 may be modified to allow the user to access other menus before ablation, but the interface may prohibit some menu functionality during ablation so that the user must monitor the lesion progress.

Figure 4:
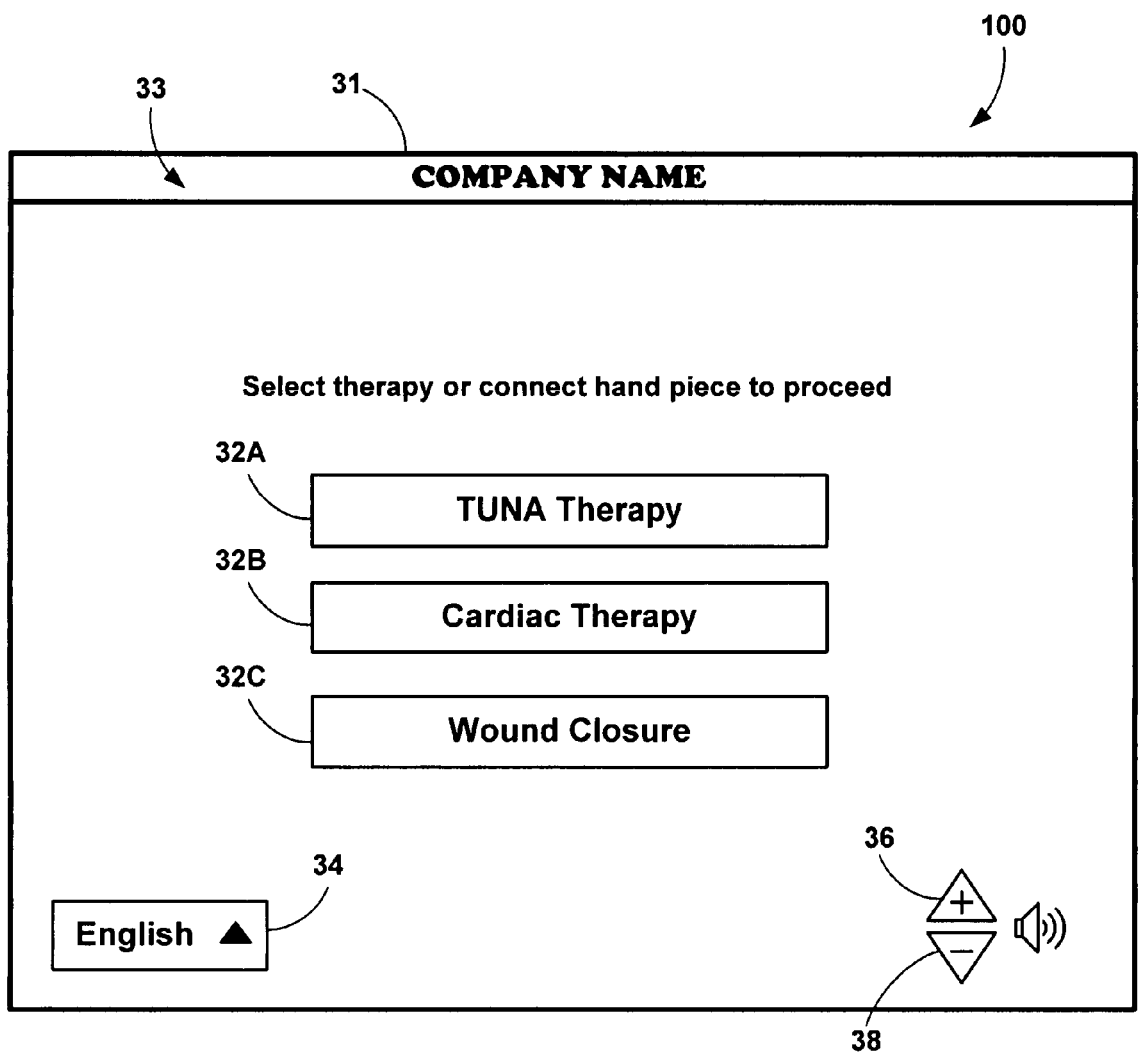
FIG. 4 is an exemplary screen shot of the main menu provided by the user interface of the ablation system.

FIG. 4 is an exemplary screen shot of the main menu provided by the user interface. As shown in FIG. 4, user interface 100 includes a menu screen 31. All boxed items in the following screens are interactive, meaning that the user may touch that portion of the user interface 100, i.e., touchscreen, to select that item. Although the following sample screen shots are used in this embodiment, any number of variations may be made to user interface 100 and retain described functionality in different forms. As described above, user interface 100 may be easily modified to utilize pointing devices, keyboards, or other input mechanisms that enable the user to interact with the user interface.

Menu screen 31 provides a few options for the user, including therapy boxes 32A, 32B and 32C (collectively "therapy boxes 32"). Therapy box 32A indicates that "TUNA Therapy," or prostate ablation, would be accessed and a new screen would be provided if the user pressed box 32A. The user may alternatively select therapy box 32B to begin a "Cardiac Therapy" ablation procedure or therapy box 32C to begin a "Wound Closure" ablation procedure during surgery. In other embodiments, other therapy boxes 32 may be present to select the most appropriate therapies. These options may be dependent upon the device or devices connected to PTD 14 or the software package available in PTD 14. When the user selects a box, that therapy program is initialized and the user is presented with a new therapy screen. An icon, symbol, image, brand, or any other information may also be included within therapy boxes 32 as appropriate. Alternatively, a smart chip included in a device coupled to PTD 14 may automatically trigger the correct software package to load. In this case, menu screen 31 may not be needed to begin therapy.

Language box 34 may reside at the lower left hand corner of the screen. The selected language may be indicated, as English is shown in box 34. If the user desires to change the language in the user interface, pressing the box may bring up another menu which includes other supported languages. Selecting one of those languages displayed may immediately change the language used in the interface. In some embodiments, English may always be the default language. Other embodiments may save the default language as the last selected language from box 34.

Volume may also be modified on the main menu screen, if available. Volume up triangle 36 may increase the volume one level for each time it is selected. Alternatively, volume triangle 38 may decrease the volume one level for each time it is pressed. Upon a volume change, an audible note may be played at the newly selected volume level. In some embodiments, a numeric indicator of the volume level may be shown for a certain period of time upon a volume change. In other embodiments, the shape of triangle 136 may be a square, circle, oval, or any other shape. Alternatively, in addition to, or in place of controlling volume, menu screen 31 may allow the user to adjust the contrast, brightness, or other visual parameters defining the look of user interface 100.

Menu screen 31 may also include other information or parameters that can be accessed by the user. For example, menu screen 31 may allow the user to adjust limits on lesion size, ablation time, ablation power, fluid flow, or any other therapy parameter. The user may also be able to access a help menu which provides detailed information for the user, trouble shooting guides, compatible devices to PTD 14, software installed in PTD 14, or PTD usage information. Other information related to ablation therapy and the use of PTD 14 may also be provided to the user.

In addition, menu screen 31 of user interface 100 includes header 33. Header 33 may include the name and/or logo of the company that manufactured PTD 14. In other embodiments, header 33 may include the marketing name of the specific ablation procedure provided by PTD 14. In addition, the name of patient 12, the date, the time of day, or any other information may be present within header 33.

Figure 5:
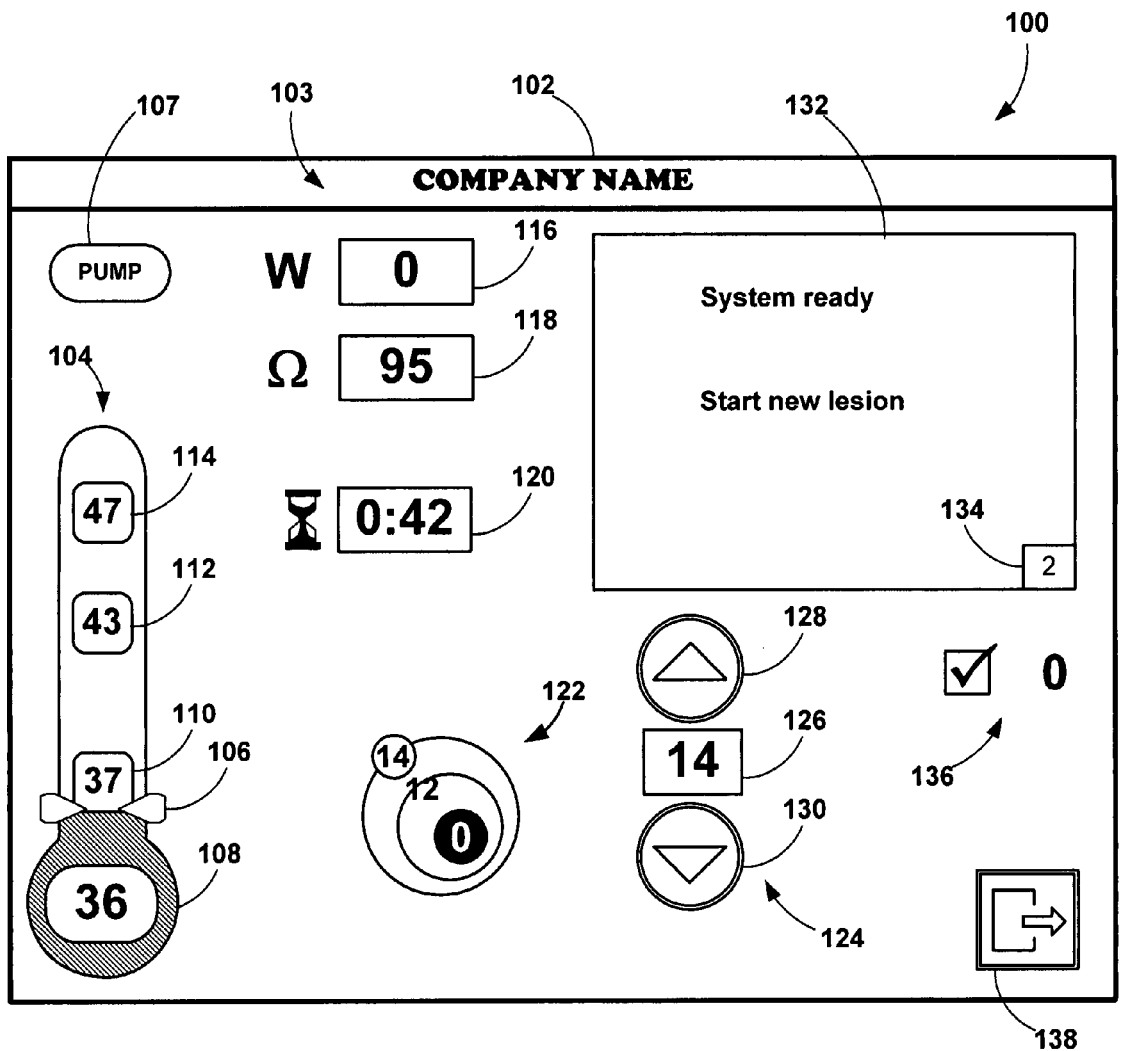
FIG. 5 is an exemplary screen shot of the initial delivery screen when the system becomes operational.

FIG. 5 is an exemplary screen shot of the initial delivery screen when the system becomes operational. As shown in FIG. 5, user interface 100 presents therapy screen 102 to the user. Therapy screen 102 includes header 103, thermometer icon 104, pump button 107, power indicator 116, resistance indicator 118, timer 120, VED icon 122, depth select 124, message box 132, lesion counter 136, and exit 138. In this embodiment, the user begins therapy by pressing a button on ablation device 20. However, other embodiments may include a start button on therapy screen 102.

Once the user opens therapy screen 102, the user selects the VED by using the depth select 124. In other words, user interface 100 may receive the ablation user input via depth select 124. The user may press down button 130 to decrease the VED value or press up button 128 to increase the VED value. Value box 126 provides a numerical indication of the selected VED value, shown as 14. In accordance with depth select 124, VED icon 122 changes to show the circle associated with the selected VED. As shown in FIG. 5, the VED value is 14, so VED icon 122 displays circles 12 and 14. The circle of 14 is the target circle that ablation therapy is directed to reach. Alternatively, the user may directly select the target circle of VED icon 122 by pointing to a desired circle or dragging the size of the circles to determine the size of the lesion. In this manner, user interface 100 receives the ablation user input via VED icon 122. Only nested circles within the selected VED are shown in VED icon 122. Each circle is labeled with the appropriate VED value as a reference for the user.

Virtual electrode depth does not indicate an actual depth of a needle electrode of ablation device 20. Since the effective heating area of a wet electrode may be increased or decreased by adjusting the flow of fluid to the needle and the time energy is applied, physically adjusting the needle length is not necessary. Therefore, the virtual electrode depth is a guide for the user to define wet electrode parameters similar to the user of dry electrode needle ablation systems that changed the length of the needle electrode according to the size of the lesion to be created. User interface 100 allows for the VED value to vary between 12 and 22, in increments of 2. These settings are related to dry electrode needle depths of 12 millimeters (mm) to 22 mm. However, knowledge of dry electrodes is not necessary to the operation of system 10 or the use of user interface 100. Indeed, the VED value may still be intuitive for the user when determining the lesion size necessary to treat patient 12. In other embodiments, user interface 100 may allow for VED values less than or greater than the VED range of 12-22. In other words, the lesion size that may be created by system 10 and represented by VED icon 122 is not limited to the example of FIG. 5. The VED range may be accordingly changed to represent the capabilities of system 10 or the predetermined lesion limits of the system. The available VED value range may be changed according to the tissue that will be ablated. In addition, user interface 100 may allow the user to select intervals smaller than 2. However, the VED values available for selection are limited by the capabilities of ablation system 10.

VED values selected by the user may be based upon the size of the prostate of patient 12. Specifically, an imaging modality, e.g., a magnetic resonance imaging (MRI) machine, may be used to visually identify the prostate and measure the outside diameter of the torus-shaped prostate gland. The user may use a table like Table 1 below as an example reference in order to match the outside diameter (OD) in millimeters (mm) of the prostate to the VED value in mm for therapy. In alternative embodiments, the user may select a time for ablation instead of a VED value. In this case, the VED values of 12-22 may be replaced with times between 20 and 180 second, for example.

TABLE 1

| VED Value (mm) | OD (mm) |
|---|---|
| 12 | 36 |
| 12, 14 | 36-40 |
| 14, 16 | 40-44 |
| 16, 18 | 44-48 |
| 18, 20 | 48-52 |
| 20, 22 | 52-56 |
| 22 | 56-80 |

Thermometer icon 104 represents the urethral temperature of patient 12. Thermometer icon 104 includes slider 106, number value 108, and temperature guides 110, 112 and 114. Damaging the tissue of the urethra is generally undesirable, the user usually desires to monitor the urethra temperature and stop ablation if the temperature becomes greater than a predetermined threshold. An alternative to stopping ablation involves irrigating the urethra with a fluid that reduces the urethra temperature. Monitoring the urethra temperature allows the user to determine when to provide this irrigation. In some embodiments, system 10 automatically irrigates the urethra when the temperature reaches a predetermined threshold. In addition, a fluid pump may be provided and controlled by system 10 to deliver the irrigation when needed or requested. Number value 108 represents the current temperature of the urethra as a number in degrees Celsius. As therapy increases the temperature of the urethra, slider 106 will move up the thermometer icon 104 according to the measured temperature. Slider 106 will slide past the temperature guides to visually indicate the urethral temperature. Temperature guide 110 is set at 37 degrees Celsius, approximately normal patient 12 temperature. Temperature guide 112 is set at 43 degrees Celsius to indicate that the urethra is getting warm. Temperature guide 114 is set at 47 degrees Celsius and indicates that the urethra is too hot and ablation will be automatically stopped.

In addition to numerical temperature values and slider 106, a third temperature representation is provided by thermometer icon 104. Thermometer icon 104 changes color beneath slider 106 as the temperature changes. When the temperature is within safe conditions, i.e., 37-43 degrees Celsius, thermometer icon 104 is blue. As the temperature increases, the color will change color. Between 43-47 degrees, thermometer icon 104 will change to orange to warn the user of heating the urethra. The user or ablation system 10 may flush the urethra with cool saline to reduce the temperature. Once the temperature reaches 47 degrees Celsius, the thermometer icon 104 turns red in color, indicating that the urethra is too hot. In this case, ablation therapy may be automatically shut down to prevent damage to the urethra. In other embodiments, different colors may represent temperature changes or more gradual changes in color may be provided. Alternatively, the entire thermometer may change color, above and below slider 106.

In some embodiments, thermometer icon 104 may represent the temperature of another tissue in patient 12. For example, thermometer icon 104 may represent the temperature of the center of the created lesion to ensure that the tissue is reaching the desired ablation temperature. In other embodiments, thermometer icon 104 may represent the temperature of a tissue at the border of the desired final lesion and be used to stop the ablation therapy. Alternatively, user interface 100 may provide a plurality of temperature icons 104 that each represents the temperature of a different location within patient 12.

Pump button 107 allows the user to access screen 902 (FIG. 13) which controls the fluid pump of PTD 14. Via screen 902, the user may prime fluid into or purge fluid from the needle electrode and fluid lines which link the needle electrode to the pump in PTD 14. The pump may control the conductive fluid used by system 10 to ablate tissue of user 12 using a virtual electrode. In some embodiments, the user may also select pump button 107 to access screen 902 to set limits or desired flow rates from the pump.

Power indicator 116 represents the power being delivered by ablation system 10 in Watts. Power indicator 116 reads zero when no therapy is being delivered. Resistance indicator 118 measures the electrical resistance of the tissue where the wet electrode is placed. Timer 120 indicates the remaining time required to create a lesion, in minutes and seconds. The remaining time is calculated as the difference between the time required for ablation according to the defined VED value and the elapsed time of the current therapy. In some embodiments, timer 120 may represent the elapsed time. The user may be able to configure timer 120 to represent the desired time. In the example of FIG. 5, the defined VED value of 14 corresponds to an ablation time of 42 seconds. Typically, larger VED values will require longer ablation times to create a larger lesion.

Message box 132 provides text to the user according to the status of the ablation therapy. In therapy screen 102, therapy has not begun, but the system is ready to start a new lesion. Index 134 displays a number that the user may use to reference the current text and look up more information about text in message box 132 in the ablation system manual. In some embodiments message box 132 may provide pictures to the user to better illustrate an error, suggestion, or fix for the problem. Lesion counter 136 indicates how many lesions have been created during the current therapy session. This may be necessary for patients 12 that require multiple lesions in order to treat the presented condition.

Figure 12:
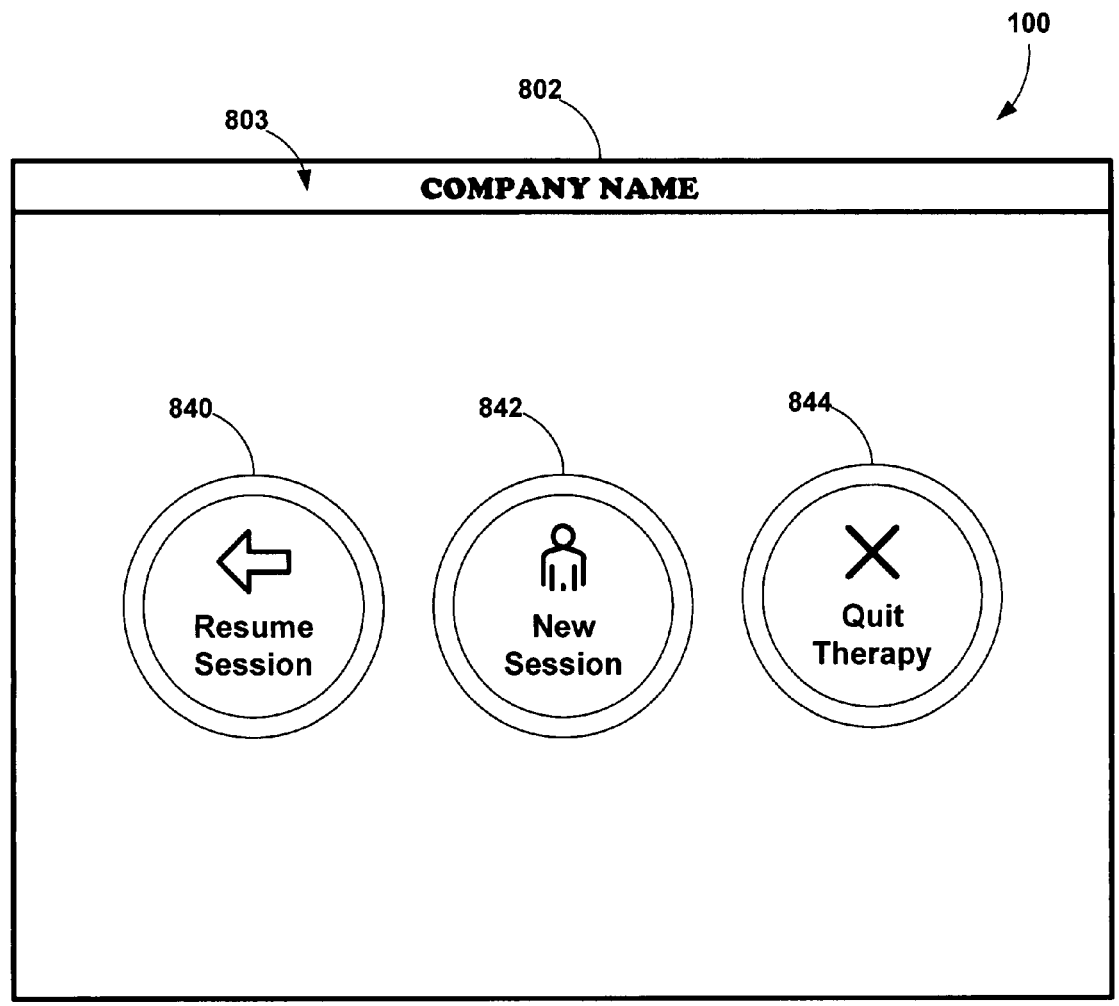
FIG. 12 is an exemplary screen shot of a session decision screen that allows the user to resume, cancel, or quit therapy.

Therapy screen 102 also includes an exit 138 to leave the therapy screen and return to a menu of user interface 100, such as menu screen 31 of FIG. 4 or decision screen 802 of FIG. 12. In some embodiments, therapy screen 102 may provide additional navigational option for the user to directly reach other screens of user interface 100. For example, therapy screen 102 may include options to enter pop-up windows that allow the user to modify some aspect of the therapy or view help information. Such menus and sub-menus are well known in the art and may be integrated into user interface 100 where appropriate.

In other embodiments, VED icon 122 may represent the virtual electrode depth without using the nested circles as shown. For example, VED icon 122 may show a representation of the needle electrode with shading around the needle electrode that changes to represent the approximate size of the lesions during ablation therapy. Alternatively, VED icon 122 may show a representation of the prostate of patient 12 with a shaded area within the prostate that corresponds to the lesion. The shaded area may increase in size as ablation therapy is delivered to patient 12. These and other variations of VED icon 122 are contemplated herein.

Figure 6:
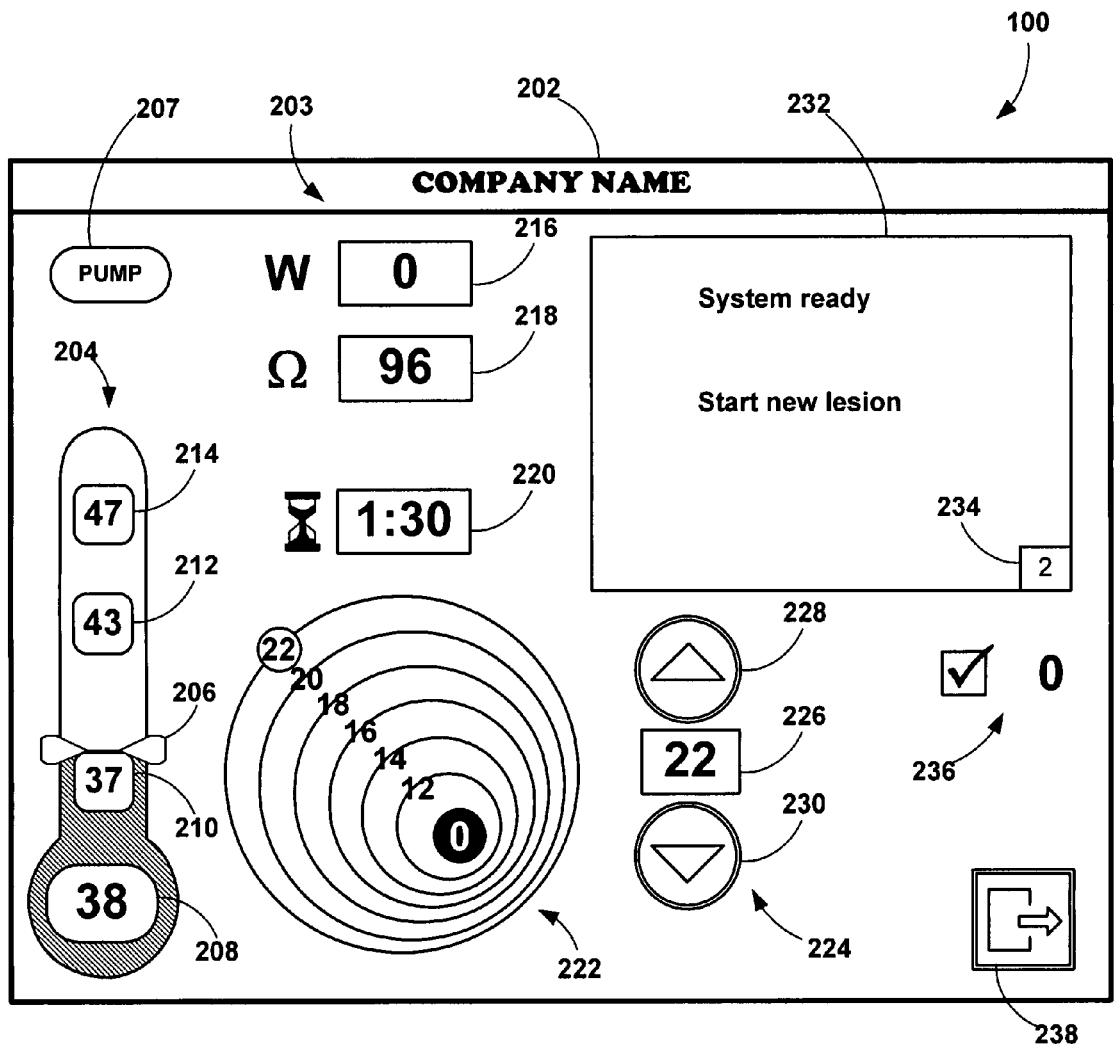
FIG. 6 is an exemplary screen shot of the delivery screen where the user can make therapy adjustments before beginning therapy.

FIG. 6 is an exemplary screen shot of the delivery screen where the user can make therapy adjustments before beginning therapy. As shown in FIG. 6, user interface 100 displays therapy screen 202. Therapy screen 202 includes header 203, thermometer icon 204, pump button 207, power indicator 216, resistance indicator 218, timer 220, VED icon 222, depth select 224, message box 232, lesion counter 236, and exit 238. Therapy screen 202 is similar to therapy screen 102 of FIG. 5, with the exception that some parameters have been changed by the user. In particular, the user has defined the VED value of 22 to create a larger lesion than indicated in therapy screen 102.

As indicated by VED icon 222, the largest VED value of 22 has been selected by the user through the use of depth select 224, and the 22 circle is the target circle for therapy. VED icon 222 shows all of the nested circles which make up the whole VED icon. The nested circles have offset centers in one direction so that the nested circles represent a three-dimensional spherical shape to the user. This three-dimensional representation may be help the user to visualize the three-dimensional lesion being created during therapy. However, some other embodiments, of VED icon 222 may have nested circles that are coaxial with common center positions.

Timer 220 indicates that it will take one minute and 30 seconds to fully create the lesion, and the timer will count down as ablation therapy progresses. Thermometer icon 204 indicates that the temperature is 38 degrees Celsius. Ablation device 20 may be placed within patient 12 prior to the user defining the VED value; therefore, probe 22 is already measuring the temperature of the urethra. Message box 232 indicates to the user that the system is ready to deliver ablation therapy to patient 12.

Figure 7:
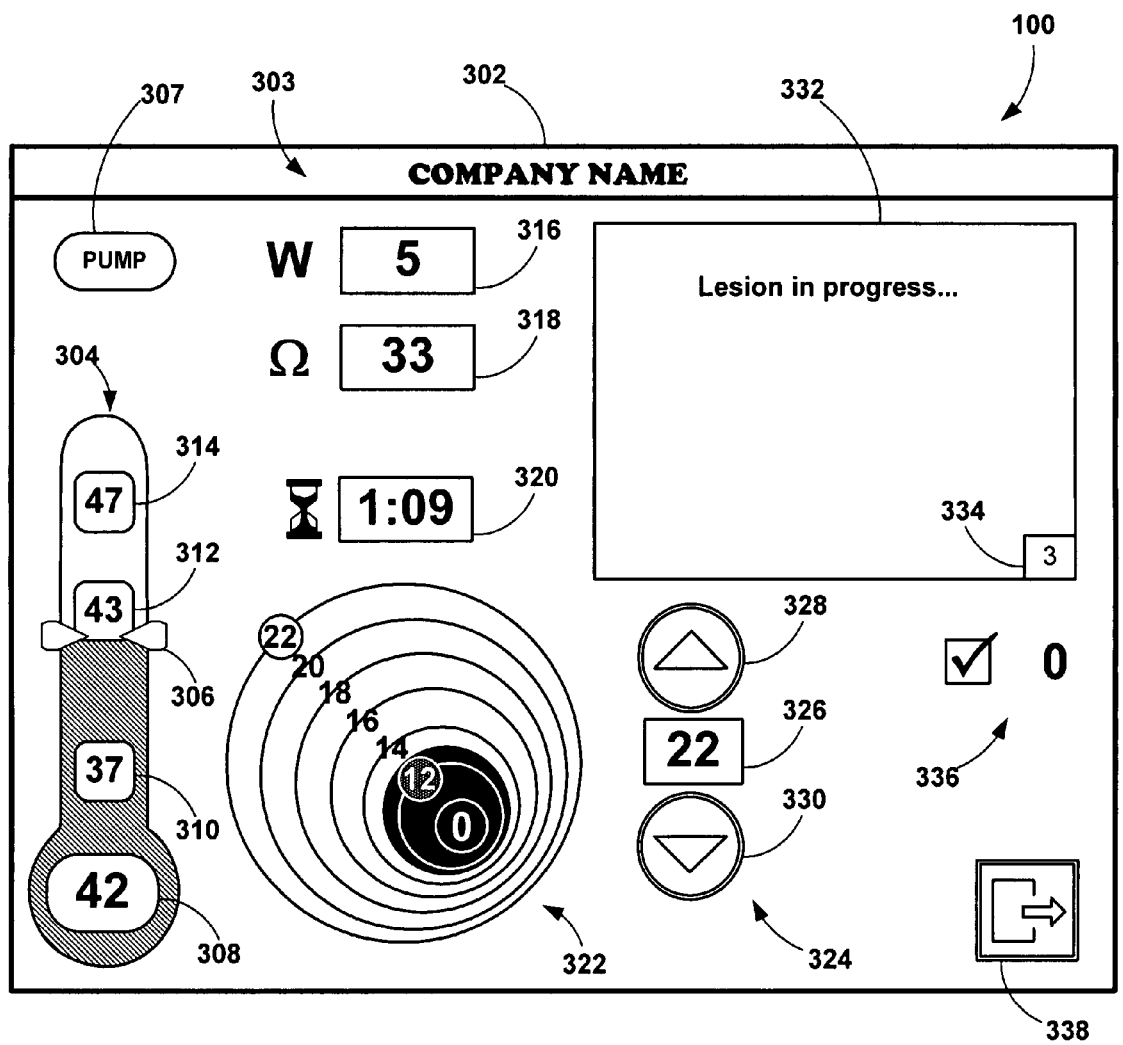
FIG. 7 is an exemplary screen shot of the delivery screen during the beginning of ablation therapy.

FIG. 7 is an exemplary screen shot of the delivery screen during the beginning of ablation therapy. As shown in FIG. 7, user interface 100 displays therapy screen 302, which shows the current status of the ablation therapy. Therapy screen 302 includes header 303, thermometer icon 304, pump button 307, power indicator 316, resistance indicator 318, timer 320, VED icon 322, depth select 324, message box 332, lesion counter 336, and stop button 338. Therapy screen 302 is similar to therapy screen 202 of FIG. 6; however, therapy screen 302 indicates that ablation therapy has begun.

Message box 332 indicates that the lesion is in progress. Power indicator 316 indicates that system 10 is producing 5 watts of power to create the lesion, and the resistance indicator 318 displays that the electrical resistance of the tissue being ablated is 33 Ohms. Thermometer icon 304 monitors the temperature of the urethra of patient 12 and indicates that the urethra temperature is at 42 degrees Celsius. At this point in the lesion creation progress, the ablation process creating the lesion is not damaging the urethral tissue.

VED icon 322 represents the current lesion progress by progressively shading the area within the nested circles of the VED icon. The shading begins at the circle labeled zero and moves outward as the lesion grows in size from the wet electrode location. The shading of VED icon 322 is orange in color, but any other color or shading markings may be used to represent the lesion size. In some embodiments, the lesion progress is not represented by shading, but a progress line that moves outward within VED icon 322. During the ablation therapy, the user may press stop button 338 to immediate shut off the ablation energy.

During ablation therapy delivery, user interface 100 may disable depth select 324 to prevent accidental changes in the VED value. In some embodiments, this disablement may be accompanied by removing or blocking out depth select 324. Alternatively, depth select 324 may continue to be operational during therapy delivery so that the user may make unanticipated changed to the therapy in real-time.

Figure 8:
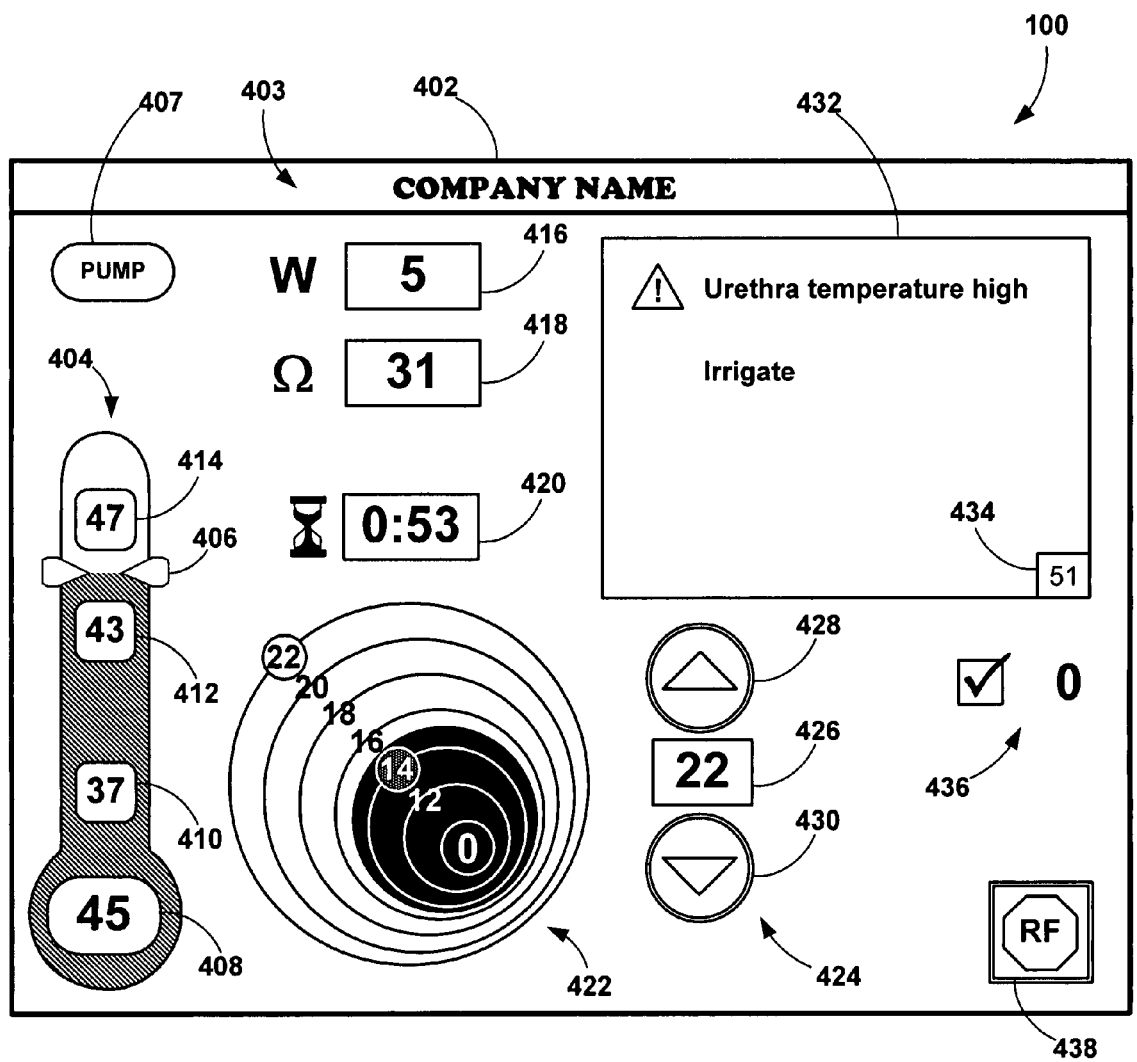
FIG. 8 is an exemplary screen shot of the delivery screen during ablation therapy when the urethra temperature nears the temperature limit.

FIG. 8 is an exemplary screen shot of the delivery screen during ablation therapy when the urethra temperature nears the temperature limit. As shown in FIG. 8, user interface 100 displays therapy screen 402. Therapy screen 402 includes header 403, thermometer icon 404, pump button 407, power indicator 416, resistance indicator 418, timer 420, VED icon 422, depth select 424, message box 432, lesion counter 436, and stop button 438. Therapy screen 402 displays lesion progress, similar to therapy screen 302 of FIG. 6. VED icon 422 continues to progressively shade the circles of the icon according to the lesion progress. Timer 420 also displays that only 53 seconds remain to create the lesion defined by the VED value.

Therapy screen 402 illustrates that the urethra temperature is high and in danger of destroying tissue. Thermometer icon 404 represents that the temperature of the urethra is 45 degrees Celsius, higher than the recommended temperature of 43 degrees Celsius. In addition to number value 408, slider 406 has moved to indicate the higher temperature and the color of thermometer icon 404 is orange. Since the urethra temperature is too high, message box 432 displays to the user that the urethra temperature is high. In addition, message box 432 suggests that the user should irrigate the urethra with cool saline or water to reduce the temperature of the urethra without stopping therapy delivery.

Figure 9:
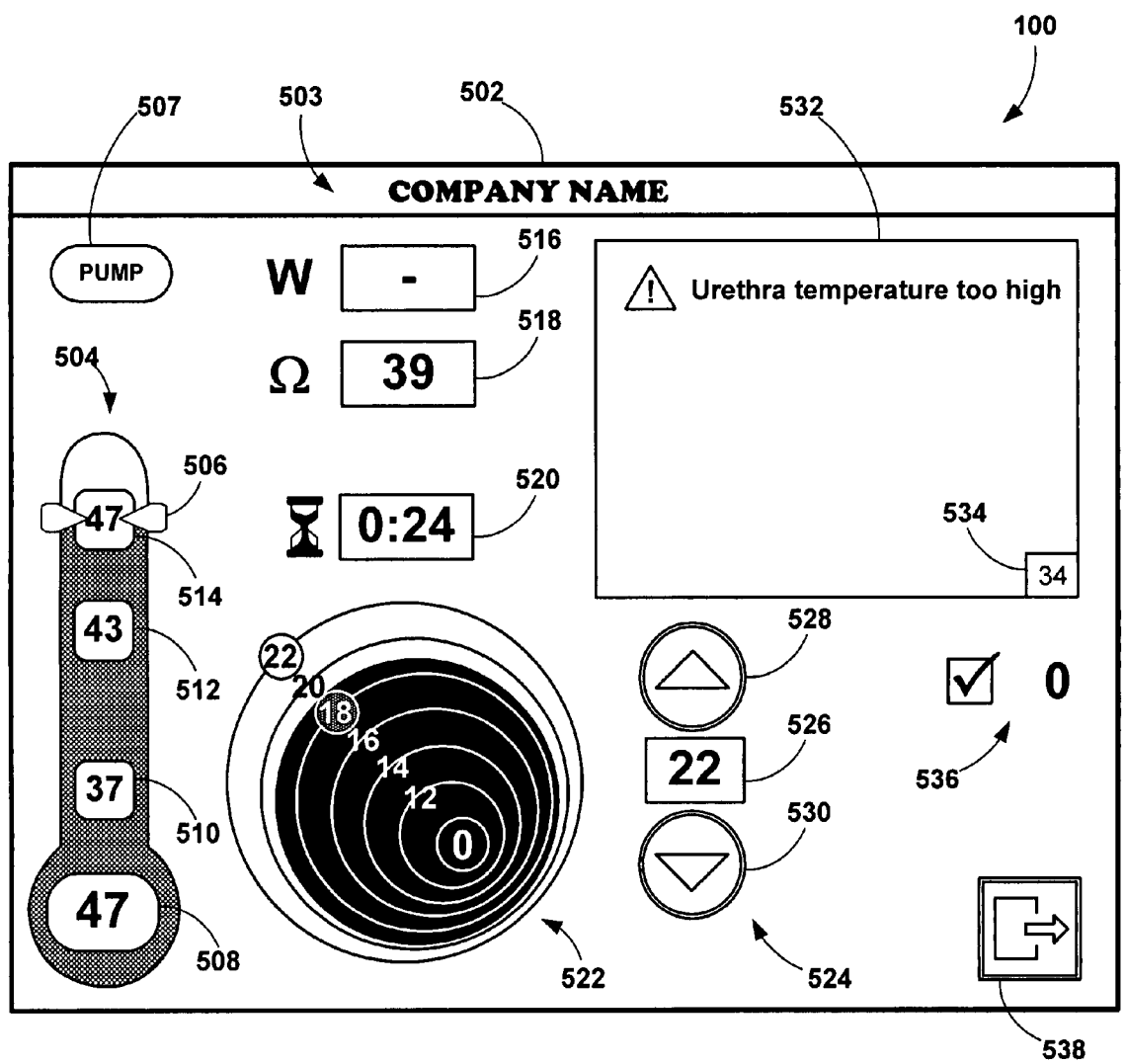
FIG. 9 is an exemplary screen shot of the delivery screen after ablation therapy is stopped due to a high urethra temperature.

FIG. 9 is an exemplary screen shot of the delivery screen after ablation therapy is stopped due to a high urethra temperature. As shown in FIG. 9, user interface 100 displays therapy screen 502. Therapy screen 502 includes header 503, thermometer icon 504, pump button 507, power indicator 516, resistance indicator 518, timer 520, VED icon 522, depth select 524, message box 532, lesion counter 536, and exit 538. Therapy screen 502 is similar to therapy screen 402 of FIG. 8. Therapy screen 502 indicates that ablation therapy has been shut off due to a high urethra temperature.

Message box 532 presents text to the user that indicates the urethra temperature is too high. Thermometer icon 504 is red in color to indicate that the urethra temperature has exceeded the safe temperature threshold, and slider 506 also indicates the high temperature of 47 degrees Celsius. In some embodiments, system 10 may not automatically shut off therapy when a temperature exceeds a threshold. For example, message box 532 may suggest that the user stop therapy when the threshold has been reached.

VED icon 522 displays the lesion progress that has been made before stopping the ablation power. The shading illustrates that the lesion was not made as large as the user wanted. The premature therapy stoppage is also evident by the remaining time of 24 seconds displayed on timer 520. In other embodiments, therapy screen 502 may display other information about the lesion after therapy is prematurely stopped.

Once ablation therapy is prematurely stopped, user interface 100 does not allow the user to restart therapy from the stopped point in the therapy. Accordingly, lesion counter 536 may change to indicate that one lesion has been created, even if the lesion was incomplete. If the user desired to continue therapy, the user must begin creating a new lesion with new parameters. In other embodiments, user interface 100 may allow the user to restart the therapy when the urethra temperature drops to a safe level where therapy can be restarted. Alternatively, system 10 automatically pauses therapy delivery when the temperature reaches an unsafe threshold and restarts the therapy when the temperature becomes cooler once more.

In some embodiments, user interface 100 may provide more options for the user. User interface 100 in any FIGS. 4-9 may contain additional features which could be modified to the user's preferences. For example, the user may decide to change the color scheme of the indicators, modify the volume, or request other available information to be displayed during therapy. In addition, the user may desire user interface 100 to be password protected in some instances.

In alternative embodiments of FIG. 9, the temperature of the urethra may remain below the safe temperature threshold and ablation therapy continues for the entire ablation time. When this occurs, VED icon 522 will be shaded out the circle labeled 22 to indicate to the user that a complete lesion has been created. Message box 532 may also indicate to the user that "lesion was created successfully" or some other representative text. Lesion counter 536 may also increase the displayed number by one. Therefore, lesion counter 536 may indicate to the user that one lesion has been created during the current ablation therapy session.

While the screen shots provided in FIGS. 4 though 9 show one type of display for use with PTD 14, many other display formats may be used. These formats may include more or less user modifications, different sized indicators, different colors, pop-up messages, or any other format for displaying the described information pertinent to this RF ablation therapy or any other therapy described herein. Alternative screens of user interface 100 are provided in FIGS. 10 and 11.

Figure 10:
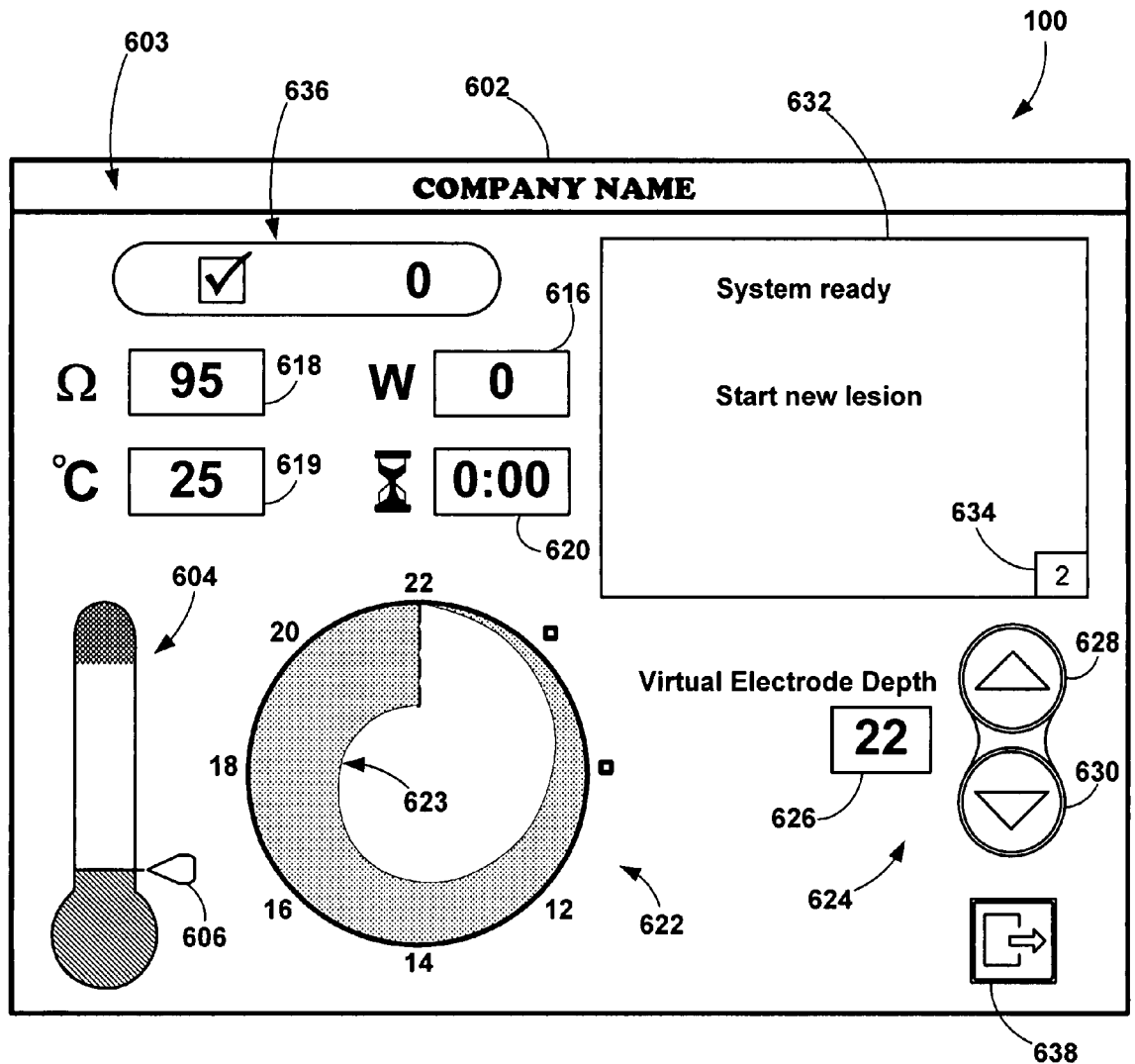
FIG. 10 is an exemplary screen shot of the delivery screen where the user can make therapy adjustments before beginning therapy, similar to FIG. 6.

FIG. 10 is an exemplary screen shot of therapy screen 602 where the user can make therapy adjustments before beginning therapy, similar to therapy screen 202 of FIG. 6. However, therapy screen 602 includes VED icon 622 which shows an increasing virtual electrode depth as ablation progresses with time. As shown in FIG. 10, user interface 100 presents therapy screen 602 to the user. Therapy screen 602 includes header 603, thermometer icon 604, power indicator 616, resistance indicator 618, temperature indicator 619, timer 620, VED icon 622, depth select 624, message box 632, lesion counter 636, and exit 638. In this embodiment, the user begins therapy by pressing a button on ablation device 20. However, other embodiments may include a start button on therapy screen 602.

Once the user opens therapy screen 602, the user selects the VED by using the depth select 624. In other words, user interface 100 may receive the ablation user input via depth select 624. The user may press down button 630 to decrease the VED value or press up button 628 to increase the VED value. Value box 626 provides a numerical indication of the selected VED value, shown as 22. In accordance with depth select 624, VED icon 622 changes to show the spiral ramped depth 623 associated with the selected VED. Ramped depth 623 of VED icon 622 is located between the spiral and the outer circle of the VED icon. As shown in FIG. 10, the VED value is 22, so VED icon 622 displays the ramped depth 623 full in the circle. If the VED value is smaller, the shaded ramped depth 623 would move counter-clockwise to become smaller to match the selected VED value. Alternatively, the user may directly move the ramped depth 623 of VED icon 622 to determine the size of the lesion. In this manner, user interface 100 may receive the ablation user input via VED icon 622. The numbers shown around the outer circumference of ramped depth 623 indicate the size of the desired lesion.

Thermometer icon 604 represents the urethral temperature of patient 12. Thermometer icon 104 includes slider 106 that moves up or down to indicate the temperature of the urethra. Temperature indicator 619 represents the current temperature value of the urethra as a number in degrees Celsius. As therapy increases the temperature of the urethra, slider 106 will move up the thermometer icon 104 according to the measured temperature. Slider 106 will slide to visually indicate the urethral temperature. Thermometer icon 604 may have two shaded areas at the low temperature and high temperature to allow the user a quick reference without needing to read a numerical value. As long as the slider is between the upper and lower shaded areas, ablation may continue as needed.

In some examples, thermometer icon 604 may change in color as the temperature of the urethra changes, similar to thermometer icon 204 of FIG. 6. For example, when the temperature is within safe conditions, i.e., 37-43 degrees Celsius, thermometer icon 604 is blue. As the temperature increases, the color will change color. Between 43-47 degrees, thermometer icon 604 will change to orange to warn the user of heating the urethra. The user or ablation system 10 may flush the urethra with cool saline to reduce the temperature. Once the temperature reaches 47 degrees Celsius, the thermometer icon 604 turns red in color, indicating that the urethra is too hot. In this case, ablation therapy may be automatically shut down to prevent damage to the urethra. In other embodiments, different colors may represent temperature changes or more gradual changes in color may be provided. Alternatively, the entire thermometer may change color, above and below slider 606.

In some embodiments, thermometer icon 604 may represent the temperature of another tissue in patient 12. For example, thermometer icon 604 may represent the temperature of the center of the created lesion to ensure that the tissue is reaching the desired ablation temperature. In other embodiments, thermometer icon 604 may represent the temperature of a tissue at the border of the desired final lesion and be used to stop the ablation therapy. Alternatively, user interface 100 may provide a plurality of temperature icons 104 that each represents the temperature of a different location within patient 12.

Power indicator 616 represents the power being delivered by ablation system 10 in Watts. Power indicator 616 reads zero when no therapy is being delivered. Resistance indicator 618 measures the electrical resistance of the tissue where the wet electrode is placed. Timer 620 indicates the remaining time required to create a lesion, in minutes and seconds. The remaining time is calculated as the difference between the time required for ablation according to the defined VED value and the elapsed time of the current therapy. In some embodiments, timer 620 may represent the elapsed time. The user may be able to configure timer 620 to represent the desired time. In the example of FIG. 10, the defined VED value of 22 corresponds to an ablation time of one minute and thirty seconds. Typically, larger VED values will require longer ablation times to create a larger lesion.

Message box 632 provides text to the user according to the status of the ablation therapy. In therapy screen 602, therapy has not begun, but the system is ready to start a new lesion. Index 634 displays a number that the user may use to reference the current text and look up more information about text in message box 632 in the ablation system manual. In some embodiments message box 632 may provide pictures to the user to better illustrate an error, suggestion, or fix for the problem. Lesion counter 636 indicates how many lesions have been created during the current therapy session. This may be necessary for patients 12 that require multiple lesions in order to treat the presented condition.

Therapy screen 602 also includes an exit 638 to leave the therapy screen and return to a menu of user interface 100, such as menu screen 31 of FIG. 4 or decision screen 802 of FIG. 12. In some embodiments, therapy screen 602 may provide additional navigational option for the user to directly reach other screens of user interface 100. For example, therapy screen 602 may include options to enter pop-up windows that allow the user to modify some aspect of the therapy or view help information. Such menus and sub-menus are well known in the art and may be integrated into user interface 100 where appropriate.

Figure 11:
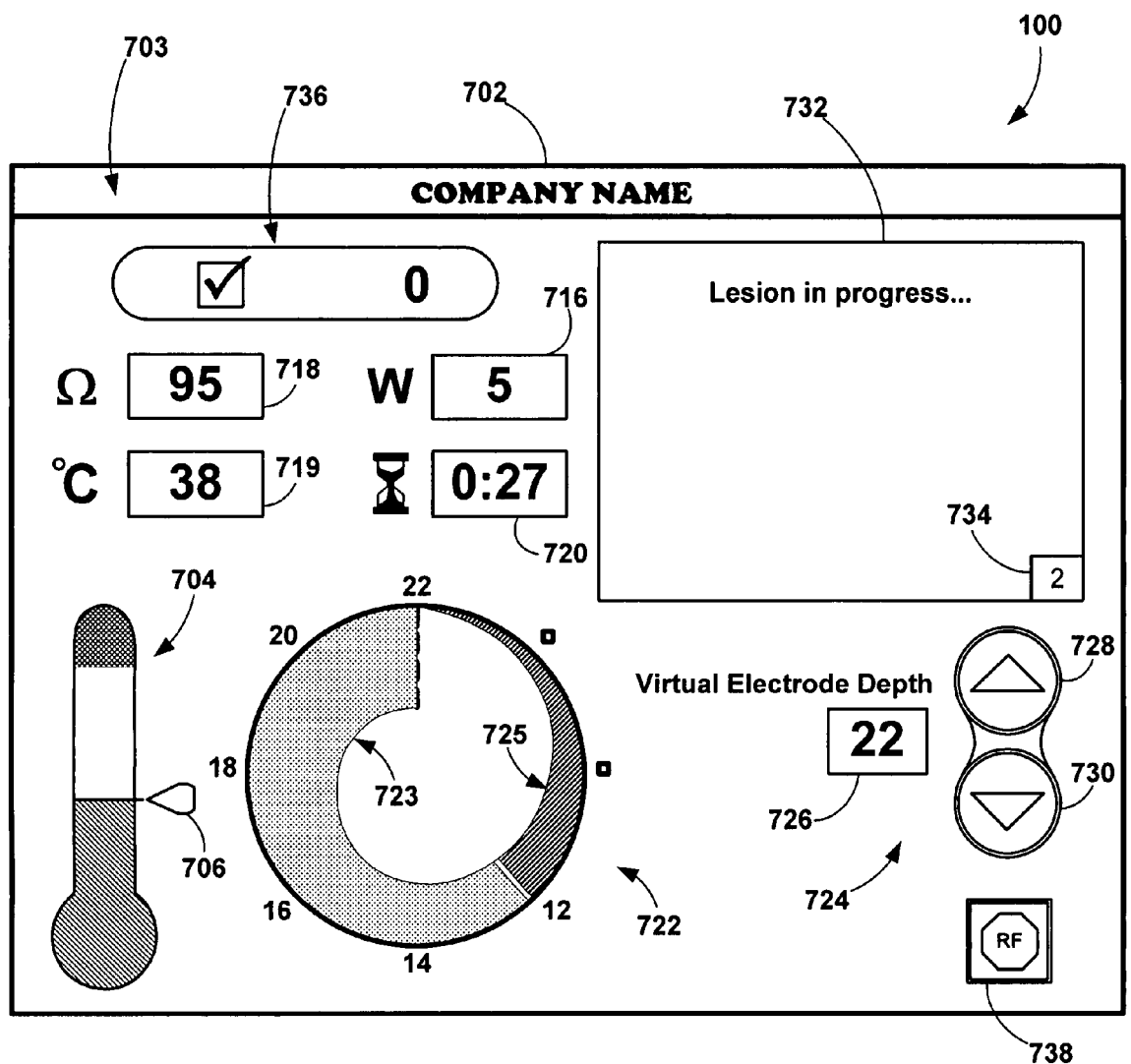
FIG. 11 is an exemplary screen shot of the delivery screen during the beginning of ablation therapy, similar to FIG. 7.

FIG. 11 is an exemplary screen shot of the delivery screen during the beginning of ablation therapy, similar to FIG. 7. As shown in FIG. 7, user interface 100 displays therapy screen 702, which shows the current status of the ablation therapy. Therapy screen 702 includes header 703, thermometer icon 704, power indicator 716, resistance indicator 718, temperature indicator 719, timer 720, VED icon 722, depth select 724, message box 732, lesion counter 736, and stop button 738. Therapy screen 702 is similar to therapy screen 602 of FIG. 10; however, therapy screen 702 indicates that ablation therapy has begun.

Message box 732 indicates that the lesion is in progress. Power indicator 716 indicates that system 10 is producing 5 watts of power to create the lesion, and the resistance indicator 718 displays that the electrical resistance of the tissue being ablated is 95 Ohms. According to timer 720, only 27 seconds remain to create the full lesion. Thermometer icon 704 and temperature indicator 719 monitors the temperature of the urethra of patient 12 and indicates that the urethra temperature is at 38 degrees Celsius. At this point in the lesion creation progress, the ablation process creating the lesion is not damaging the urethral tissue.

VED icon 722 represents the current lesion progress by progressively shading the ramped depth 723 of VED icon 722. The current lesion size is indicated by lesion ramp 725 which progressively shades in ramped depth 723 toward the target position of the virtual electrode depth, e.g., 22 or until the ablation is stopped. Lesion ramp 725 may be orange or some other color or pattern to distinguish the difference between ramped depth 723 and lesion ramp 725. During the ablation therapy, the user may press stop button 738 to immediate shut off the ablation energy. Once the lesion is created, lesion counter 736 may increase the lesion count from 0 to 1.

During ablation therapy delivery, user interface 100 may disable depth select 724 to prevent accidental changes in the VED value. In some embodiments, this disablement may be accompanied by removing or blocking out depth select 724. Alternatively, depth select 724 may continue to be operational during therapy delivery so that the user may make unanticipated changed to the therapy in real-time.

FIG. 12 is an exemplary screen shot of a session decision screen that allows the user to resume, cancel, or quit therapy. As shown in FIG. 12, decision screen 802 of user interface 100 includes header 803, resume button 840, new button 842, and quit button 844. Additional buttons may be provided to allow the user to enter other screens or continue with therapy in some other manner. There may also be a help button so that the user may inquire about how to trouble shoot problems or treat patient 12.

A user may enter decision screen 802 after selecting any of exits 138, 238, 338, 538, and 638. The user may select to resume the currently selected therapy by selecting resume button 840. The user may select to begin a new session for therapy by selecting new button 842. In addition, the user may select to quit the currently selected therapy and return to menu screen 31 by selecting quit button 844. In some examples, user interface 100 may provide a pop-up window after the user makes a selection. The pop-up window may prompt the user to confirm the selection or allow the user to return to decision screen 802 without performing the selected action.

Figure 13:
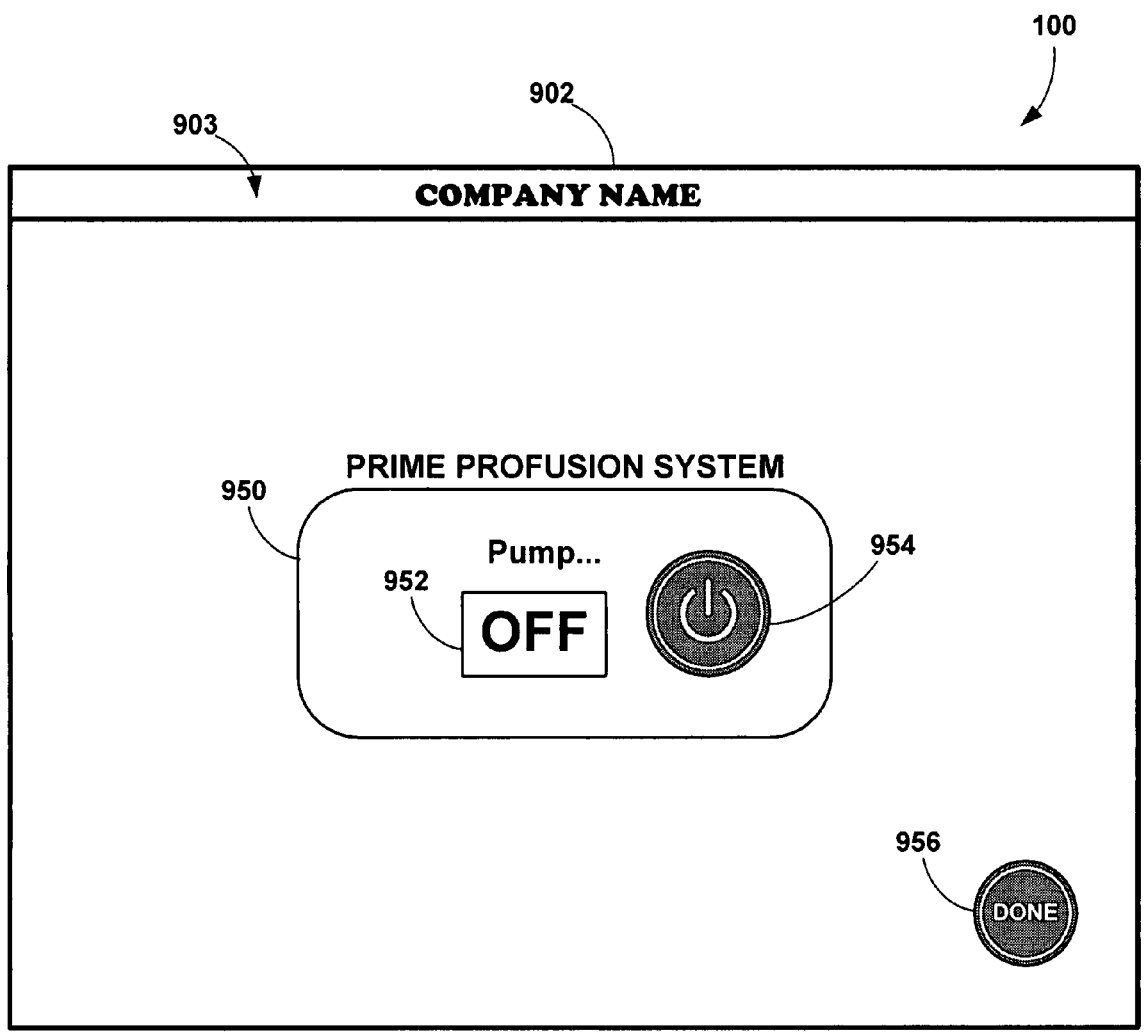
FIG. 13 is an exemplary screen shot of a pump screen that allows the user to prime the fluid perfusion system used during ablation.

FIG. 13 is an exemplary screen shot of a pump screen that allows the user to prime the fluid perfusion system used during ablation. As shown in FIG. 13, user interface 100 includes pump screen 902 that provides header 903, pump icon 950, status icon 952, power button 954, and done button 956. The user may access screen 902 via any therapy screen of user interface 100 in order to control the pump of PTD 14. The pump may control the conductive fluid used by system 10 to ablate tissue of user 12 using a virtual electrode.

The user may initially prime fluid through the pump, fluid lines, and needle electrode by selecting power button 954 to turn on the pump. When the pump is running, status icon 952 changes to "ON" so that the user knows fluid is flowing through system 10. When the pump is primed, the user may again select power button 954 to turn the pump off which is indicated by "OFF" in pump icon 952. In addition, screen 902 may provide other icons and/or buttons that allow the user to set pump limits, flow rate limits, pump run times, tubing inner diameters, attached needle electrodes, or any other parameters of system 10 related to the flow of the conductive fluid to patient 12.

Various embodiments of the described invention may include processors that are realized by microprocessors, Application-Specific Integrated Circuits (ASIC), Field-Programmable Gate Arrays (FPGA), or other equivalent integrated logic circuitry. The processor may also utilize several different types of storage methods to hold computer-readable instructions for the device operation and data storage. These memory and storage media types may include a type of hard disk, random access memory (RAM), or flash memory, e.g. CompactFlash or SmartMedia. Each storage option may be chosen depending on the embodiment of the invention. While the implantable IMD 18 may contain permanent memory, external programmer 16 may contain a more portable removable memory type to enable easy data transfer for offline data analysis.

The preceding specific embodiments are illustrative of the practice of the invention. It is to be understood, therefore, that other expedients known to those skilled in the art or disclosed herein may be employed without departing from the invention or the scope of the claims. Many embodiments of the invention have been described. Various modifications may be made without departing from the scope of the claims. These and other embodiments are within the scope of the following claims.

The invention claimed is:

1. A method comprising:
   receiving ablation user input from a user defining a virtual electrode depth; and
   representing the virtual electrode depth of an ablation device as a virtual electrode depth icon on a display, wherein:
   the virtual electrode depth icon is configured to progressively shade an area of the virtual electrode depth icon according to an ablation therapy progress,
   the virtual electrode depth is indicative of at least one of a flow of fluid and a time that energy is applied for the ablation therapy progress, and
   the virtual electrode depth icon comprises a plurality of nested circles.

2. The method of claim 1, wherein the plurality of nested circles have offset centers that represent a three-dimensional shape.

3. The method of claim 1, further comprising progressively shading the virtual electrode depth icon according to the ablation therapy progress, wherein progressively shading the virtual electrode depth icon comprises starting shading at the center of an innermost circle of the nested circles and continuing shading progressively outward towards a target circle of the virtual electrode depth.

4. A tangible computer-readable medium comprising instructions that cause a processor to:
   receive ablation user input from a user defining a virtual electrode depth;

represent the virtual electrode depth of an ablation device as a virtual electrode depth icon on a display; wherein:
the virtual electrode depth icon is configured to progressively shade an area of the virtual electrode depth icon according to an ablation therapy,
the virtual electrode depth is indicative of at least one of a flow of fluid and a time that energy is applied for the ablation therapy, and
the instructions that cause the processor to represent the virtual electrode depth comprise instructions that cause the processor to represent the virtual electrode depth icon as a plurality of nested circles with offset centers; and
progressively shade the virtual electrode depth icon according to the ablation therapy progress by starting to shade at the center of an innermost circle of the nested circles and continuing to shade progressively outward towards a target circle of the virtual electrode depth.

5. A method comprising:
receiving ablation user input from a user defining a virtual electrode depth; and
representing the virtual electrode depth of an ablation device as a virtual electrode depth icon on a display, wherein the virtual electrode depth icon is configured to progressively shade an area of the virtual electrode depth icon according to an ablation therapy progress, and wherein the virtual electrode depth icon comprises a plurality of nested circles.

6. The method of claim 5, wherein the plurality of nested circles have offset centers that represent a three-dimensional shape.

7. The method of claim 5, further comprising progressively shading the virtual electrode depth icon according to the ablation therapy progress, wherein progressively shading the virtual electrode depth icon comprises starting shading at the center of an innermost circle of the nested circles and continuing shading progressively outward towards a target circle of the virtual electrode depth.

8. The method of claim 5, wherein the virtual electrode depth icon is labeled with unique virtual electrode depth values at specific locations of the virtual electrode depth icon.

9. The method of claim 5, further comprising delivering ablation therapy with the ablation device according to the virtual electrode depth from the user.

10. The method of claim 5, further comprising representing a patient temperature as a thermometer icon on the display, wherein representing the patient temperature as a thermometer icon comprises representing a current temperature with at least one of a number value, a slider, and a color on the thermometer icon.

11. The method of claim 5, further comprising representing a text status message, a current therapy energy, a tissue electrical resistance, and a remaining time on the display, wherein the remaining time is calculated as a difference between a required ablation time based upon the virtual electrode depth and an elapsed time.

12. The method of claim 5, wherein receiving ablation user input comprises identifying a location on the display touched by the user that corresponds to defining the virtual electrode depth.

13. A tangible computer-readable medium comprising instructions that cause a processor to:
receive ablation user input from a user defining a virtual electrode depth; and
represent the virtual electrode depth of an ablation device as a virtual electrode depth icon on a display; wherein the virtual electrode depth icon is configured to progressively shade an area of the virtual electrode depth icon according to an ablation therapy, and wherein the instructions that cause the processor to represent the virtual electrode depth comprise instructions that cause the processor to represent the virtual electrode depth icon as a plurality of nested circles with offset centers.

14. The tangible computer-readable medium of claim 13, further comprising instructions that cause the processor to progressively shade the virtual electrode depth icon according to the ablation therapy progress by starting to shade at the center of an innermost circle of the nested circles and continuing to shade progressively outward towards a target circle of the virtual electrode depth.

15. The tangible computer-readable medium of claim 13, further comprising instructions that cause the processor to deliver ablation therapy with the ablation device according to the virtual electrode depth from the user.

* * * * *